(12) United States Patent
Groux et al.

(10) Patent No.: US 7,771,932 B1
(45) Date of Patent: Aug. 10, 2010

(54) METHOD FOR IDENTIFICATION OF TR1 LYMPHOCYTES REGULATORS BY THE PRESENCE AND OVER-EXPRESSION OF SPECIFIC MOLECULES AND APPLICATION THEREOF

(75) Inventors: Hervé Groux, Le Rouret (FR); Arnaud Foussat, Biot (FR)

(73) Assignee: TxCell, Nice (FR)

( * ) Notice: Subject to any disclaimer, the term of this patent is extended or adjusted under 35 U.S.C. 154(b) by 542 days.

(21) Appl. No.: 10/561,517

(22) PCT Filed: Jun. 24, 2004

(86) PCT No.: PCT/FR2004/001583

§ 371 (c)(1),
(2), (4) Date: Nov. 30, 2007

(87) PCT Pub. No.: WO2005/000344

PCT Pub. Date: Jan. 6, 2005

(30) Foreign Application Priority Data

Jun. 24, 2003 (FR) .................................. 03 07601

(51) Int. Cl.
C12Q 1/68 (2006.01)
G01N 33/53 (2006.01)
C12N 5/0783 (2010.01)
(52) U.S. Cl. ............................ 435/6; 435/7.1; 435/325; 435/326; 424/93.1
(58) Field of Classification Search ........................ None
See application file for complete search history.

(56) References Cited

FOREIGN PATENT DOCUMENTS

| WO | WO 2005/046729 | 5/2005 |
|---|---|---|
| WO | WO 2006/018674 | 2/2006 |

OTHER PUBLICATIONS

Mottet et al., "Cutting Edge: Cure of Colitis by CD4+CD25+ Regulatory T Cells[1]", Apr. 15, 2003, pp. 3939-3943, XP-002275079.
Groux et al., "A CD4+ T-cell subset inhibits antigen-specific T-cell responses and prevents colitis", Oct. 1997, pp. 737-742, Nature/vol 389.
Barrat et al., In Vitro Generation of Interleukin 10-producing Regulatory CD4+ T Cells Is Induced by Immunosuppressive Drugs and INhibited by T Helper Type 1 (Th1)- and Th2-inducing Cytokines, Mar. 4, 2002, pp. 603-616, The Rockefeller University Press, vol. 195, No. 5.
Groux, "Type 1 T-Regulatory Cells: Their Role in the Control of Immune Responses[1]", May 15, 2003, pp. 8S-12S, Transplantation, vol. 75, No. 9, Supplement, XP-008025406.
Mallat et al., "Induction of a Regulatroy T Cell Type 1 Response Reduces the Development of Atherosclerosis in Apolipoprotein E-Knockout Mice", Jul. 21, 2003, pp. 1232-1237, Basic Science Reports, XP009028370.
Blackman et al., "A role for clonal inactivation in T cell tolerance to Mis-1$^a$", Jun. 7, 1990, pp. 540-542, Nature, vol. 345.
Jones et al., "Peripheral Clonal Elimination of Funtional T Cells", Dec. 21, 1990, pp. 1726-1729, Science, vol. 250.
Röcken et al., "Immune Deviation—the Third Dimension of Nondeletional T Cell Tolerance", 1996, pp. 175-194, Immunological Reviews, ISSN 0105-2896.
Webb, et al. "Extrathymic Tolerance of Mature T Cells: Clonal Elimination as a Consequence of Immunity", Dec. 21, 1990, pp. 1249-1256, Cell, vol. 63.
Huang et al., "Cell growth and matrix invasion of EBV-immortalized human B lymphocytes is regulated by expression of $\chi_v$ integrins", Feb. 2000, pp. 1915-1923, Oncogene (2000) 19.
Sawitzki et al., "Regulatory Tolerance-Mediating T Cells in Transplantation Tolerance", 2001, pp. 2092-2093, Transplantation Proceedings, 33.
Springer, "Traffic Signals for Lymphocyte Recirculation and Leukocyte Emigration: The Multistep Paradigm", Jan. 28, 1994, pp. 301-314, Cell, vol. 76.
Bour et al., "In Vitro T Cell Response to Staphylococcal Enterotoxin B Superantigen in Chronic Plaque Type Psoriasis", 1995, pp. 218-221, Scandinavian University Press.
Weiner, "Oral Tolerance for the Treatment of Autoimmune Diseases", 1997, pp. 341-351, Annu. Rev. Med. 48.
Powrie et al., "Inhibition of Th1 Responses Prevents Inflammatory Bowel Disease in scid Mice Reconstituted with CD45RB$^{hi}$ CD4+ T Cells", Oct. 1994, pp. 553-562, Immunity, vol. 1.
Alon et al., "From rolling to arrest on blood vessels: leukocyte tap dancing on endothelial integrin ligands and chemokines at sub-second contacts", 2002, pp. 93-104, seminars in Immunology, vol. 14.
Kubes, "Introduction: The complexities of leukocyte recruitment", 2002, pp. 65-72, seminars in Immunology, vol. 14.
Ticchioni et al., "Integrin-associated protein (CD47/IAP) contributes to T cell arrest on inlammatory vascular endothelium under flow", Feb. 2001, pp. 341-350, The FASEB Journal, vol. 15.
Butcher et al., "Lymphocyte Homing and Homeostasis", Apr. 5, 1996, pp. 60-66, Science, vol. 272.
Foussat et al., "A Comparative Study between T Regulatory Type 1 and CD4+ CD25+ T Cells in the Control of Inflammation",.2003, pp. 5018-5026, The Journal of Immunology.
Wakkach et al., "Differentiation of Regulatory T Cells 1 Is Induced by CD2 Costimulation[1]", 2001, pp. 3107-3113, The Journal of Immunology.

(Continued)

Primary Examiner—James Martinell
(74) Attorney, Agent, or Firm—Young & Thompson

(57) ABSTRACT

The invention relates to a method for identification of Tr1 lymphocyte regulators in a biological sample, based on the determination of the simultaneous presence of the molecular group CD4, CD18 and/or CD11a, CD49b and, where appropriate, by the demonstration of an over-expression of genes coding for the molecules CD4, PSGL-1, PECAM-1 and alphaV/beta3. The invention further relates to a method of quantification and a prognostic or diagnostic method for autoimmune or inflammatory diseases, based on said identification method. The invention also relates to an enrichment method for Tr1 lymphocyte regulators, based on the determination of the simultaneous presence of said molecules and, finally, an enriched composition from said enrichment method, for the treatment of an auto-immune or inflammatory disease, in particular Crohn's disease.

30 Claims, 15 Drawing Sheets

OTHER PUBLICATIONS

Figure 1:
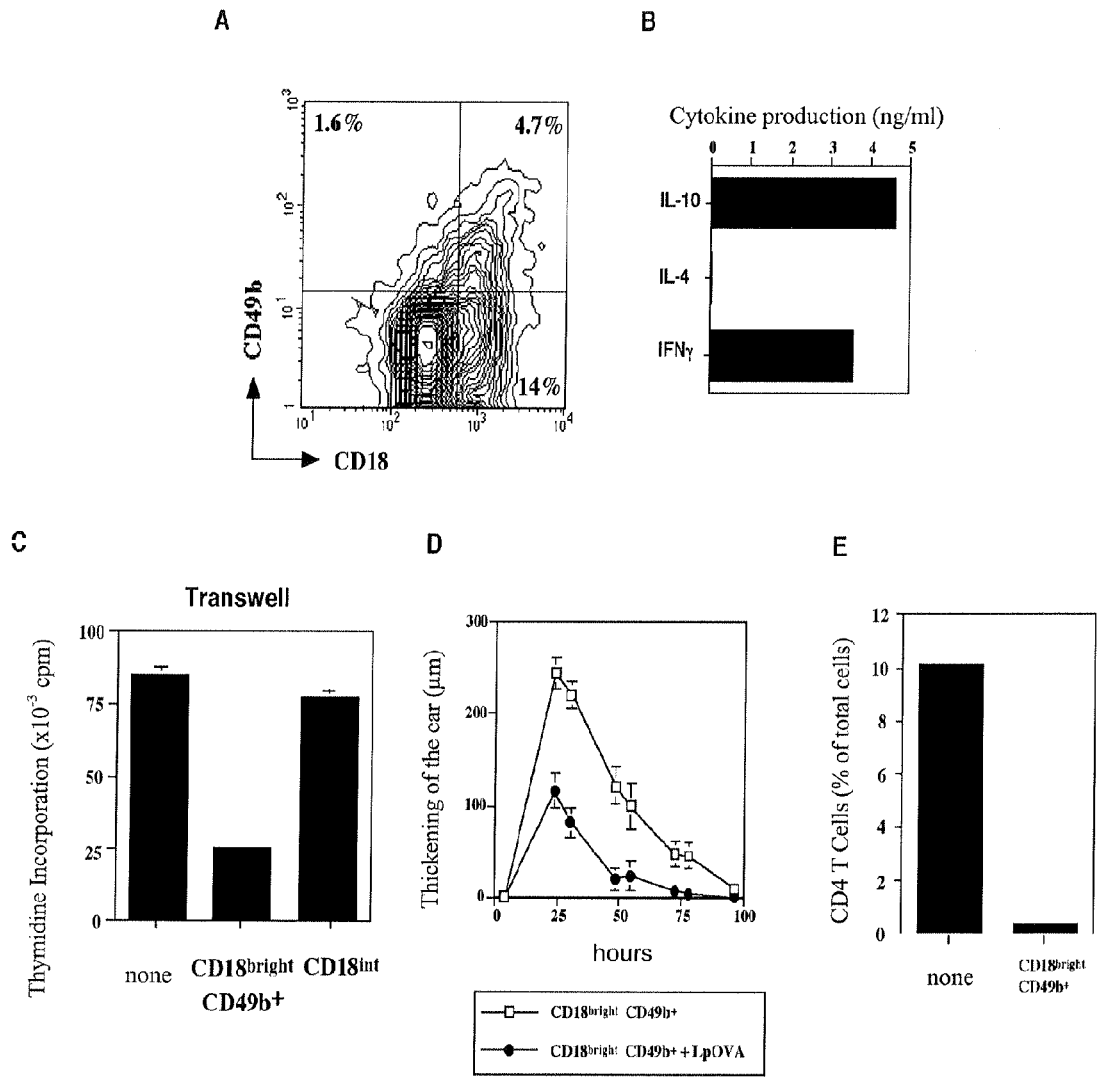

Campbell, "Chemokines and the Arrest of Lymphocytes Rolling Under Flow Conditions", Jan. 16, 1998, pp. 381-384, Science, vol. 279.

Chen et al., "Regulatory T Cell Clones Induced by Oral Tolerance: Suppression of Autoimmune Encephalomyelitis", Aug. 26, 1994, pp. 1237-1240, Science, vol. 265.

Mc Guirk et al., "Pathogen-specific T Regulatroy 1 Cells Induced in the REspiraotry Tract by a Bacterial Molecule that Stimulates Interleukin 10 Production by Dendritic Cells: A Novel Strategy for Evasion of Protective T Helper Type 1 Responses by *Bordetella pertussis*", Jan. 21, 2002, pp. 221-231, The Rockefeller University Press, vol. 195, No. 2.

Asserman et al., "An Essential Role for Interleukin 10 in the Function of Regulatory T Cells That Inhibit Intestinal Inflammation", Oct. 4, 1999, pp. 995-1003, The Rockefeller University Press, vol. 190, No. 7.

Jones, "Failure of Clonal Deletion in Neonatally Thymectomized Mice: Tolerance Is Preserved through Clonal Anergy", Nov. 1990, pp. 127-1285, The Journal of Experimental Medicine, vol. 172.

Hirata, "P-Selection Glycoprotein Ligand 1 (PSGL-1) Is a Physiological Ligand for E-Selectin in Mediating T Helper 1 Lymphocyte Migration", Dec. 4, 2000, pp. 1669-1675, The Rockefeller University Press, vol. 192, No. 11.

Kehren et al., "Cytotoxicity Is Mandatory for CD8[+] T Cell-mediated Contact Hypersensitivity", Mar. 1, 1999, pp. 779-786, The Rockefeller University Press, vol. 189, No. 5.

Graca et al., "Identification of Regulatory T Cells in Tolerated Allografts", Jun. 17, 2002, pp. 1641-1646, The Rockefeller University Press, vol. 195, No. 12.

Cong et al., "Bacterial-Reactive T Regulatory Cells Inhibit Pathogenci Immune Responses to the Enteric Flora[1]", 2002, pp. 6112-6119, The Journal of Immunology.

Leuker et al., "Neonatally Induced Inactivation of the Vascular Cell Adhesion Molecule 1 Gene Impairs B Cell Localization and T Cell-dependent Humoral Immune Response", Mar. 19, 2001, pp. 755-767, The Rockefeller University Press, vol. 193, No. 6.

Powrie et al., "Regulatory Interaction between $CD45RB^{high}$ and $CD45RB^{low}$ CD4[+] T Cells Are Important for the Balance between Protective and Pathogenic Cell-mediated Immunity", Feb. 1994, pp. 589-600, The Rockefeller University Press, vol. 179.

Cottrez et al., "Quantitative PCR: validation of the use of a multispecific internal control", May 25, 1994, pp. 2712-2713, Nucleic Acids Research, vol. 22, No. 13, Oxford University Press.

Groux et al., "Regulatory T cells and inflammatory bowel disease", Oct. 1999, pp. 442-445, Viewpoint Immunology Today.

Lecart et al., "Phenotypic Characterization of Human CD4[+] Regulatory T Cells Obtained from Cutaneous Dinitrochlorobenzene-Induced Delayed Type of Hypersensitivity Reactions", 2001, pp. 1-8, The Society for Investigative Dermatology, Inc.

Cottrez et al., "T Regulatory Cells 1 Inhibit a Th2-Specific Response in Vivo[1]", 2000, The American Association of Immunologists, pp. 4848-4853.

Kitani et al., "Activated Self-MHC-Reactive T Cells Have the Cytokine Phenotype of Th3/T Regulatory Cell 1 T Cells", 2000, The American Association of Immunologists, pp. 691-702.

Constantin et al., "Chemokines Trigger Immediate β2 Integrin Affinity and Mobility Changes: Differential Regulation and Roles in Lymphocyte Arrest under Flow", Dec. 2000, pp. 759-769, Immunity, vol. 13.

PCT Transmission in French and Written Opinion translated in English.

Letter in French with search report and Written Opinion translated in English.

METHOD FOR IDENTIFICATION OF TR1 LYMPHOCYTES REGULATORS BY THE PRESENCE AND OVER-EXPRESSION OF SPECIFIC MOLECULES AND APPLICATION THEREOF

This invention relates to a method for identifying Tr1-regulatory lymphocytes in a biological sample based on the determination of the simultaneous presence of the group of CD4, CD18 and/or CD11a, CD49b molecules and, where applicable, by the demonstration of an overexpression of genes encoding molecules CD4, PSGL-1, PECAM-1 and alphaV/beta3. The invention also relates to a quantification method and a method for prognosis or diagnosis of autoimmune or inflammatory diseases based on said identification method. The invention also relates to a method for Tr1-regulatory lymphocyte enrichment based on the determination of the simultaneous presence of these molecules. Finally, the invention relates to the use of an enriched composition according to said enrichment method for treating an autoimmune or inflammatory disease, in particular Crohn's disease.

Immune tolerance is obtained by various mechanisms enabling the system to distinguish itself from foreign bodies. In addition, the immune system is exposed to repeated non-pathogenic antigen stimulations. To prevent undesired cell activations and chronic inflammations, the immune system has mechanisms that cooperate to maintain tolerance, involving anergic T cells (Blackman et al., 1990, Nature 345, 540-542; Jones et al, 1990b, J Exp Med 172, 1277-1285), the inactivation of T cells by apoptosis (Jones et al, 1990a, Science 250, 1726-1729; Webb et al, 1990, Cell 63, 1249-1256), and active immune suppression (Rocken et al, 1996, Immunol Rev 149, 175-194; Weiner et al, 1997, Annu Rev Med 48, 341-351). Active immune suppression is mediated by specialized T cells of which the function is to suppress the proliferation and activation of effective T cells. Recent studies have demonstrated that regulatory cells designated Tr1 belong to CD4+ T cells (Chen et al, 1994, Science 265, 1237-1240; Groux et al., 1997, Nature 389, 737-742; Mc Guirck et al, 2002, J Exp Med 195, 221-231; Powrie et al, 1994, J Exp Med 179, 589-600), and that their function is dependent on the presence of IL-10 (Asseman et al, 1999, J Exp Med 190, 995-1004; Barrat et al, 2002 J Exp Med 195, 603-616; Groux et al, 1997) and TGF-β (Groux et al, 1997; Kitani et al, 2000, J Immunol 165, 691-702).

Among the T CD4+ lymphocytes, also referred to as T helpers, 2 main types of T helpers are distinguished: Th1 lymphocytes, involved in the development of the cellular immune response, produce proinflammatory cytokines such as interleukin-2 (IL-2) and interferon gamma (IFNγ) and have macrophage-activating effects; Th2 lymphocytes, which produce cytokines such as interleukins IL-4, IL-6, IL-10 and IL-13, promote antibody secretion.

In the thymus, the central tolerance is a well-established mechanism that involves a deletion of autoreactive T cells after interaction with dendritic cells (DC) derived from bone marrow.

However, the mechanisms by which the Tr cells form in vivo and exercise their immunoregulatory effects have yet to be defined and are the subject of intense research.

In particular, some autoimmune and/or inflammatory diseases involve Tr1 cells.

Autoimmune diseases are caused by a deregulation of the immune system, which involves an undesirable immune response of the body with respect to its own antigens. Attempts have been made to manipulate the antigens at the source of these diseases or the aggressive T cells specific to these antigens, but the results obtained have often been very limited, in particular by the lack of knowledge of all of the antigens involved in the disease concerned. Indeed, the so-called autoantigens, or the antigens responsible for inflammatory and autoimmune disorders, are still not known, or differ from one individual to another (due to genetic inheritance).

The treatments currently used for these diseases are either palliative treatments (insulin for diabetes, antihistamines for allergic disorders) or systemic treatments with anti-inflammatories (NSAIDs) and/or immunosuppressants (glucocorticoids, cyclosporin, antibodies, and so on). Therefore, there is clearly a need for a powerful immunosuppressant treatment, but it should be limited to the organ affected or more specifically to the hyperactive area of the immune system.

Tr1 cells, when they are restimulated by the antigen used for their induction, proliferate little, produce very large amounts of IL-10, very small amounts of IL-2, and do not produce IL-4. When activated Tr1 cells are cultivated in the presence of other T CD4+ cells, they suppress the proliferation of the latter in response to an antigen; this effect results from the secretion of cytokines, and in particular IL-10, by the Tr lymphocytes, and not a direct action of the latter on the T CD4+ cells; it can therefore be obtained without having to recognize the antigen responsible for the proliferation of these cells. This presents a significant advantage in the case of autoimmune diseases, for which a treatment can be considered without requiring knowledge of the exact antigen against which the pathogenic cells are directed.

It has thus been observed, in an experimental model of Crohn's disease in the mouse, in which the proinflammatory cells are directed against resident bacteria of the digestive flora, that the administration to animals of Tr1 cells directed against ovalbumin, accompanied by the administration of ovalbumin in the food, makes it possible to prevent the onset of chronic inflammation of the colon (Groux et al, 1997, Nature 389, 737-742).

Moreover, in studies on different animal models of Crohn's disease, multiple sclerosis, or graft versus host reaction, the inventors showed that the Tr1 inhibitory cells were capable not only of preventing, but also of curing these different pathologies (Foussat et al. Submitted, Barrat et al. J. Exp. Med. 2002, 4, 603).

The document MOTTET et al. (Journal of Immunology, vol. 170, no. 8, Apr. 15, 2003, pages 3939-3943) relates to the study of the capacity of CD4+CD25+ regulatory T cells, known for their role in the prevention of immune diseases mediated by T cells, to improve an established inflammation. The study shows that CD4+CD25+ T cells are capable of treating an intestinal inflammation and suggests that CD4+CD25+ T cells can be beneficial in the treatment of chronic inflammatory diseases.

Tr1 cells obtained from T cells of a patient can therefore potentially be used in the context of cellular therapy for regulating the immune response in this patient. They can also be used in particular to prevent or treat, not only the autoimmune and inflammatory diseases mentioned above, but also any other pathology characterized by an abnormal inflammatory response, such as diabetes, psoriasis, atherosclerosis, rheumatoid polyarthritis or asthma; they can also be used in the treatment of graft rejections or graft versus host reactions.

Thus, cited among the autoimmune disease in which the Tr1 cells can be used, are selected diseases in the group consisting of chronic active hepatitis, Addison's disease, antiphospholipid syndrome, atopic allergy, autoimmune atrophic gastritis, autoimmune achlorhydria, celiac disease, Crohn's disease, Cushing's syndrome, dermatomyositis, diabetes type I, discoid lupus, erythematosis, Goodpasture's syndrome, Grave's disease, Hashimoto's thyroiditis, idiopathic adrenal atrophy, insulin-dependent diabetes, Lambert Eaton syndrome, lupoid hepatitis, certain cases of lymphopenia, multiple sclerosis, pemphigus vulgaris or foliaceous, bullous pemphigoid, pernicious anemia, phacogenic uveitis, polyarthritis, primary biliary cirrhosis, primary sclerosing cholangitis, psoriasis, Reiter's syndrome, polychondritis, rheumatoid arthritis, Schmidt syndrome, scleroderma, Sjogren's syndrome, Systemic Erythematous Lupus, Takayasu's arteritis, temporal arteritis, thyrotoxicosis, type B insulin resistance, ulcerative colitis, Wegener's granulomatosis, myasthenia gravis, Guillain-Barré syndrome, autoimmune ureitis, autoimmune hemolytic anemia, autoimmune thrombocytopenia, autoimmune oophoritis, Behcet's disease, dermatitis herpetiformis, polymyositis, dermatomyositis, spondyloarthropathies such as ankylosing spondylitis, and vitiligo.

One of the difficulties in using Tr1-regulatory lymphocytes is the ability to identify them simply and with certainty from a lymphocyte population. Current techniques for identifying Tr1-regulatory lymphocytes consists of studying the cytokine production profile with a lymphocyte population capable of including Tr1-regulatory lymphocytes. In particular, Groux et al. (Nature, 389, 737-742, 1997) notes that this lymphocyte population produces very large amounts of interleukin 10 (IL-10), large amounts of TGF-$\beta$ (tumor growth factor $\beta$), very small amounts of interleukin 2 (IL-2) and does not produce interleukin 4 (IL-4). A person skilled in the art can confirm the presence of Tr1-regulatory lymphocytes in a lymphocyte population by studying the proliferative response of CD4+ T lymphocytes present in said population: when the Tr1-regulatory lymphocytes are cultivated in the presence of CD4+ T lymphocytes, they suppress the proliferation of the latter in response to an antigen (Groux et al, Nature, 389, 737-742, 1997). These identification techniques have the disadvantage of being time- and labor-intensive.

Thus, there is currently a need for a fast and effective technique for identifying the presence or absence of Tr1-regulatory lymphocytes from a sample containing a lymphocyte population. Such a method can also be advantageous because it would enable a lymphocyte population to be enriched with Tr1-regulatory lymphocytes.

This is precisely the subject of the present invention.

The invention thus relates to a method for identifying Tr1-regulatory lymphocytes present in a biological sample including lymphocytes, characterized in that it comprises the following steps:
(a) determining the simultaneous presence of expression products by said lymphocytes of genes encoding the CD4 molecule and all of the molecules of group A, wherein said group A consists of molecules CD18 and/or CD11a, and CD49b; and
(b) identifying, as Tr1-regulatory lymphocytes, the lymphocytes that simultaneously express the genes encoding the CD4 molecule and all of the molecules of group A.

By group A consisting of molecules CD18 and/or CD11a, and CD49b, we are referring to the group A consisting of:
CD18 and CD49b molecules;
CD11a and CD49b molecules; or
CD18, CD11a and CD49b molecules.

Among the biological samples containing lymphocytes in which the presence of Tr1-regulatory lymphocytes is to be identified, biological samples from peripheral blood taken from a subject, biological samples from a method for in vitro preparation of Tr1-regulatory lymphocytes from a population of cells, in particular lymphocytes, where applicable from a sample from a subject, or from progenitor cells, are preferred.

The method for identifying Tr1-regulatory lymphocytes according to this invention can be performed on any biological sample containing a lymphocyte population in which the presence of Tr1-regulatory lymphocytes is to be determined.

The subject from which the biological sample is collected can be any mammal, in particular a mouse, and preferably a human. This subject can preferably be healthy, or affected by an autoimmune or inflammatory disease. The term "healthy subject" according to the invention includes any subject, preferably human, not affected by an autoimmune or inflammatory disease. A list of autoimmune diseases is provided above; inflammatory diseases are diseases in which there is an infiltration of mononuclear cells, a proliferation of fibroblasts and new blood vessels, leading to an increase in connective tissue, and tissue destruction. Chronic inflammatory diseases of the intestine are noted in particular.

The biological sample can also be obtained from methods for in vitro preparation of Tr1-regulatory lymphocytes, which methods are well known to a person skilled in the art. These preparation methods include, for example, the method described in the publication of an inventor (Groux et al., Nature, 389, 737-742, 1997), which consists of repeatedly stimulating CD4+ T cells with the antigen in the presence of IL-10. The method for in vitro preparation of Tr1-regulatory lymphocytes described in the international patent application of an inventor, published on Nov. 21, 2002 under the number WO 02/092793 can also be cited: this method consists of placing CD4+ T lymphocytes in culture in the presence of artificial antigen-presenting cells expressing an HLA class-II molecule and the human LFA-3 (CD58) molecule, but not expressing any of the co-stimulation molecules B7-1 (CD80), B7-2 (CD86), B7-H1, CD40, CD23 and ICAM-1 (CD54). Another method for in vitro preparation of Tr1-regulatory lymphocytes is described in the following example 5, a method which consists of obtaining, in vitro, a population of human dendritic cells from human progenitor cells, which dendritic cells are capable of inducing the differentiation of human T lymphocytes into Tr1-regulatory lymphocytes.

By product for expression of a gene encoding a molecule in the method for identifying Tr1-regulatory lymphocytes according to this invention, we are referring, for each of these molecules, to the expression product of the gene encoding said molecule, which can be either the translation product of said gene, namely the peptide encoded by said gene, or the transcription product of said gene, namely the mRNA encoding said molecule. Preferably, the expression product is said molecule expressed at the surface of said lymphocytes or one of its representative fragments, namely a fragment of said molecule of which the presence at the surface of the lymphocytes makes it possible to determine the expression of this molecule at the surface of the lymphocytes (phenotype "+" for said molecule).

The inventors have indeed shown that the Tr1-regulatory lymphocytes can be identified by determining the simultaneous presence of the expression product by said lymphocytes of the gene encoding the CD4 molecule and genes coding for the molecules of group A (see examples 2 and 3).

Molecules CD11a and CD18 are associated with the surface of the lymphocytes to form the dimeric $\beta_2$-integrin CD11a/CD18, which is also referred to as LFA-1 for Lymphocytes Function Associated Antigen-1. The presence of this $\beta_2$-integrin can therefore be identified by determining the presence of the expression product by said lymphocytes of the gene encoding the CD11a molecule, of the expression product of the gene coding for the CD18 molecule, or, simultaneously, of these two expression products.

The inventors have also demonstrated that the Tr1-regulatory lymphocytes can also be identified independently of the aforementioned identification method by the overexpression of at least 1, and preferably at least 2, 3, 4 or all of the genes encoding the molecules CD11a, CD18, PSGL-1, PECAM-1 and/or alphaV/beta 3, by comparison with the expression by lymphocytes known to be type Th1 or Th2, in particular Th1 or Th2 lymphocytes from clones (see example 4).

The molecule PSGL-1, or P-selectin glycoprotein-ligand-1 is a cell adhesion molecule (CAM) belonging to the selectin family.

The molecule PECAM-1 or Platelet-Endothelial Cell Adhesion Molecule-1, also referred to as molecule CD31, is a CAM molecule belonging to the family of Ig-like molecules.

The molecule alphaV/beta3, also referred to as molecule CD51/CD61, or VNR for vitronectin receptor, is a CAM molecule belonging to the subfamily of $\beta_3$-integrins.

According to a specific embodiment of the invention, the aforementioned method for identifying Tr1-regulatory lymphocytes based on the expression of molecules of group A is characterized in that:

in step (a), the expression by said lymphocytes of at least one gene selected from the genes encoding the molecules of following group B is compared: CD11a, CD18, PSGL-1, PECAM-1 and alphaV/beta 3a, wherein said expression is compared with the expression of said same gene by Th1 or Th2 lymphocytes; and in step (b), the lymphocytes that overexpress at least one of said genes encoding the molecules of group B are identified as Tr1-regulatory lymphocytes.

By lymphocytes that overexpress at least one of the genes encoding the molecules of group B, we are referring to lymphocytes of which the expression of at least one of said genes is significantly higher than the expression of these same molecules by Th1 or Th2 lymphocytes; preferably, said overexpression by the Tr1-regulatory lymphocytes with respect to that obtained by Th1 or Th2 lymphocytes is at least 2, 3, 4, 5, 7 or 10 times higher than the expression on Th1 or Th2 lymphocytes.

Preferably, the Th1 or Th2 lymphocytes are Th1 or Th2 lymphocytes from clones normally obtained on inflammatory sites, in particular of the skin, which are differentiated in vitro in the presence of IL-4 for Th2 or IL-12 for Th1.

According to another specific embodiment of the invention, the method for identifying Tr1-regulatory lymphocytes is characterized in that, in step (a), the expression of at least two of said genes of group B is compared and in that, in step (b), the lymphocytes that overexpress said two genes of group B are identified as Tr1-regulatory lymphocytes.

According to another specific embodiment of the invention, the method for identifying Tr1-regulatory lymphocytes is characterized in that, in step (a), the expression of all of the genes of group B is compared, and in that, in step (b), the lymphocytes that overexpress all of the genes of group B are identified as Tr1-regulatory lymphocytes.

The identification method according to the invention is preferably characterized in that, in step (a), the expression of, at least three of said genes of group B is compared, and in that, in step (b), the lymphocytes that overexpress said genes of group B are identified as Tr1-regulatory lymphocytes.

The identification method according to the invention is also preferably characterized in that, in step (a), the expression of at least four of said genes of group B is compared, and in that, in step (b), the lymphocytes that overexpress the four said genes of group B are identified as Tr1-regulatory lymphocytes.

The invention can also relate to a method for identifying Tr1-regulatory lymphocytes present in a biological sample comprising lymphocytes, characterized in that it comprises the following steps:

(a) comparing the expression by said lymphocytes of at least one gene selected from the genes encoding the following molecules of group B: CD11a, CD18, PSGL-1, PECAM-1 and alphaV/beta3, wherein said expression is compared with the expression of said same gene by Th1 or Th2 lymphocytes; and (b) identifying, as Tr1-regulatory lymphocytes, the lymphocytes that overexpress at least one of said genes encoding the molecules of group B.

In addition, Tr1-regulatory lymphocytes can also be identified by the identification method according to the invention also involving the determination of the presence of the expression product by said lymphocytes of the gene encoding the CD3 molecule.

Thus, the invention also preferably relates to an identification method according to the invention characterized in that step (a) consists of determining additionally and simultaneously the presence of the expression product by said lymphocytes of the gene encoding the CD3 molecule and in that step (b) consists of identifying, as Tr1-regulatory lymphocytes, the lymphocytes that also simultaneously express the gene encoding the CD3 molecule.

According to the method of the invention, the identification of molecules at the surface of the lymphocytes can be performed using any suitable method enabling specifically the simultaneous presence of these molecules to be identified.

Among these methods, the preferred ones are methods in which the identification of these molecules at the surface of the lymphocytes is performed using polyclonal, monoclonal or recombinant antibodies or fragments thereof, or ligands, capable of specifically recognizing these molecules, these antibodies or antibody fragments which may, where appropriate, be marked.

The identification method according to the invention is preferably characterized in that, in step (a), the simultaneous presence of said molecules of group A expressed at the surface of said lymphocytes is determined.

A preferred embodiment of the identification method according to the invention is characterized in that step (a) consists of determining the simultaneous presence of said molecules expressed at the surface of said lymphocytes by means of antibodies specific to said molecules.

The antibodies specific to said molecules that can be used in the identification method according to the invention particularly include, but are not limited to, human or murine anti-CD4 antibodies such as those secreted by clones RPA-T4 and H129-19 (Becton Dickinson, Le Pont de Claix—FR), human or murine anti-CD18 antibodies such as those secreted by clones 6.7, C71/16, and Game-46 (Becton Dickinson), murine anti-CD11a antibodies such as those secreted by clone M17/4 (Biocompare, South San Francisco—US), human or murine anti-CD49b antibodies such as those secreted by clones AK-7 and Hal/29 (Becton Dickinson), anti-murine CD31 antibodies such as those secreted by clone MEC 13.3 (Becton Dickinson), and anti-human CD3 antibodies such as those secreted by clone UCHT-1 (Caltag, Burlingame, US).

As non-limiting examples of natural ligands other than antibodies capable of recognizing these molecules, the following can be cited, for example: molecule CD18 (LFA-1), hu-soluble ligands ICAM-1 (CD54), hu-ICAM-1Fc chimera, hu-ICAM-2Fc chimera (CD102), huICAM-3Fc chimera (CD50), mu-ICAM-1 (CD54), mu-ICAM-2Fc chimera (CD102), muICAM-3Fc chimera (CD50), muICAM-5Fc chimera (CD50), JAM-1, JAM-2, JAM-3; all of these ligands are available on the market (in particular R&D Systems, Minneapolis—US).

In a particularly preferred embodiment of the identification method according to the invention, the identification of molecules of which the simultaneous presence is to be determined, at the surface of lymphocytes present in said biological sample to be tested is preferably performed by immunofluorescence, or by a radioimmunological or immunoenzymatic method.

In general, for the preparation of polyclonal or monoclonal antibodies or fragments thereof, or recombinant antibodies, reference can be made to the techniques well known to a person skilled in the art, which techniques are in particular described in the manual "Antibodies" (Harlow et al., Antibodies: A Laboratory Manual, Cold Spring Harbor Publications pp. 726, 1988) or to the preparation technique using hybridomes, described by Kohler et al. (Köhler and Milstein. Nature, 256: 495-497, 1975). Antibodies specific to the method according to the invention can be obtained, for example, from serum or cells of an animal immunized specifically against these molecules.

By antibody fragment capable of recognizing specifically these molecules, we are referring in particular to antibody fragments including any fragment of said antibody capable of binding specifically to the epitope of said molecule to which the antibody from which said fragment was obtained binds. Examples of such fragments include, in particular, single-chain antibodies (scFv) or monovalent fragments Fab or Fab' and divalent fragments such as F(ab')2, which have the same binding specificity as the antibody from which they are obtained. These antibody fragments can be obtained from polyclonal or monoclonal antibodies using methods such as digestion with enzymes, such as pepsin or papain and/or by cleavage of disulfide bonds by chemical reduction. These antibodies, or their fragments, can also be obtained by genetic recombination (recombinant antibodies).

The antibodies or their fragments, capable of recognizing specifically these molecules, can also exist in the form of marked antibodies so as to obtain a signal that is directly or indirectly detectable and, preferably, quantifiable.

The marked antibodies, or fragments thereof, which can be used in the identification method according to this invention, are, for example and preferably, so-called immunoconjugated antibodies which are conjugated with fluorescent markers which include in particular fluorescein and its derivatives, such as fluorescein isothiocyanate (FITC), or allophycocyanin (APC), phycoerythrin-cyanin 5 (PC5) and phycoerythrin (PE), green fluorescent fluorescein diacetate, calcein AM, red fluorescent tetramethyl rhodamine or rhodamine and its derivatives, GFP (for Green Fluorescent Protein), dansyl, umbelliferon, and so on.

Such immunoconjugated antibodies are available on the market, in particular APC-conjugated anti-CD4 (RPA-T4, Becton Dickinson), PC5-conjugated anti-CD3 (UCHT-1, Caltag, Burlingame, US), PE-conjugated anti-CD18 (6.7, Becton Dickinson) and FITC-conjugated anti-CD49b (AK-7, Becton Dickinson) in humans, and PC5-conjugated mouse anti-CD4 (H129-19, Becton Dickinson), PE-conjugated mouse anti-CD18 (C71/16, Becton Dickinson) and FITC-conjugated mouse anti-CD49b (Hal/29, Becton Dickinson).

The marked antibodies, or fragments thereof, which can also be used in the identification method according to this invention also include immunoconjugated antibodies conjugated with enzymes such as peroxidase, alkaline phosphatase, β-D-galactosidase, glucose oxidase, glucose amylase, carbonic anhydrase, acetylcholinesterase, lysozyme, malate dehydrogenase or glucose-6 phosphate dehydrogenase or by a molecule such as biotin, digoxigenin or 5-bromo-deoxyuridine.

In such conjugates, the antibodies or their fragments can be prepared using methods known to a person skilled in the art. They can be coupled to enzymes or fluorescent markers directly or by means of a spacer group or a group of bonds as in a polyaldehyde, such as glutaraldehyde, ethylenediaminetetraacetic acid (EDTA), diethylenetriaminepentaacetic acid (DPTA), or in the presence of binding agents such as periodate, and so on. The conjugates comprising fluorescein-type markers can be prepared by reaction with an isothiocyanate.

Other conjugates can also include chemiluminescent markers such as luminol and dioxetanes or bioluminescent markers such as luciferase and luciferin.

Among the markers capable of being bound to these antibodies or their fragments that can be used in the identification method according to this invention, the following radioactive markers can be cited: $^{14}C$, $^{36}Cl$, $^{57}Co$, $^{58}Co$, $^{51}Cr$, $^{152}Eu$, $^{59}Fe$, $^{3}H$, $^{125}I$, $^{131}I$, $^{32}P$, $^{35}S$, $^{75}Se$ and $^{99m}Tc$, which can be detected by known means such as the gamma counter or scintillation counter, autoradiography, and so on.

Any conventional method depending on the formation of an antibody-molecule immune complex (antigen) can be implemented to perform such an identification. Said method, if it is radioimmunologic or immunoenzymatic, can be a competitive or a sandwich method, or any method known to a person skilled in the art.

In a particularly preferred embodiment, the determination step (a) of the identification method according to this invention is performed using antibodies marked with fluorescent markers. Again preferably, each of said antibodies or antibody fragments specific to a molecule of which the presence is to be determined, will be marked with a different marker for each of the specificities. Even more preferably, said identification method also makes it possible to quantify, in the biological sample to be tested, the number or proportion of lymphocytes simultaneously having said molecules of which the presence is to be identified, such as, to provide a non-limiting example, the identification and quantification method used in examples 2, 3 and 4 below.

According to a specific embodiment of the invention, the method is characterized in that said markers are fluorescent and are selected from the group consisting of fluorescein isothiocyanate (FITC), allophycocyanin (APC), phycoerythrin-cyanin 5 (PC5), phycoerythrin (PE), green fluorescent fluorescein diacetate, calcein AM and red fluorescent tetramethyl rhodamine.

The identification methods that can be used include the FACS (fluorescence-activated cell sorter) technique, which consists of an electronic system for separating the cells according to their size and the intensity of the fluorescence that they emit after various markings. The apparatus prepares microdrops of the cell suspension, which are diluted so that they contain only one cell. The microdrop passes before a laser light beam and the cells are analyzed (histogram) and separated on the basis of their fluorescence and/or their size.

In a preferred embodiment, the identification method according to the invention is characterized in that, in step (a), the determination of the simultaneous presence of said molecules of group A expressed at the surface of said lymphocytes is implemented by flow cytometry.

The term flow cytometry refers to any technique enabling cells to be counted and measured, in particular the FACS technique as described above.

When the determination step (a) of the identification method according to this invention is performed using fluorescent immunoconjugates (such as fluorescent antibodies), it is preferable to use an identification method according to the invention in which, in step (a) of said method, the CD18 molecule is determined as being present at the surface of said lymphocytes when the fluorescence intensity level obtained for this molecule corresponds to that obtained for the same molecule at the surface of monocyte cells ("CD18bright").

According to a preferred embodiment, the identification method according to the invention is characterized in that, in step (a) of said method, the presence of a CD18bright fluorescence intensity is determined for the CD18 molecule.

Figure 15:
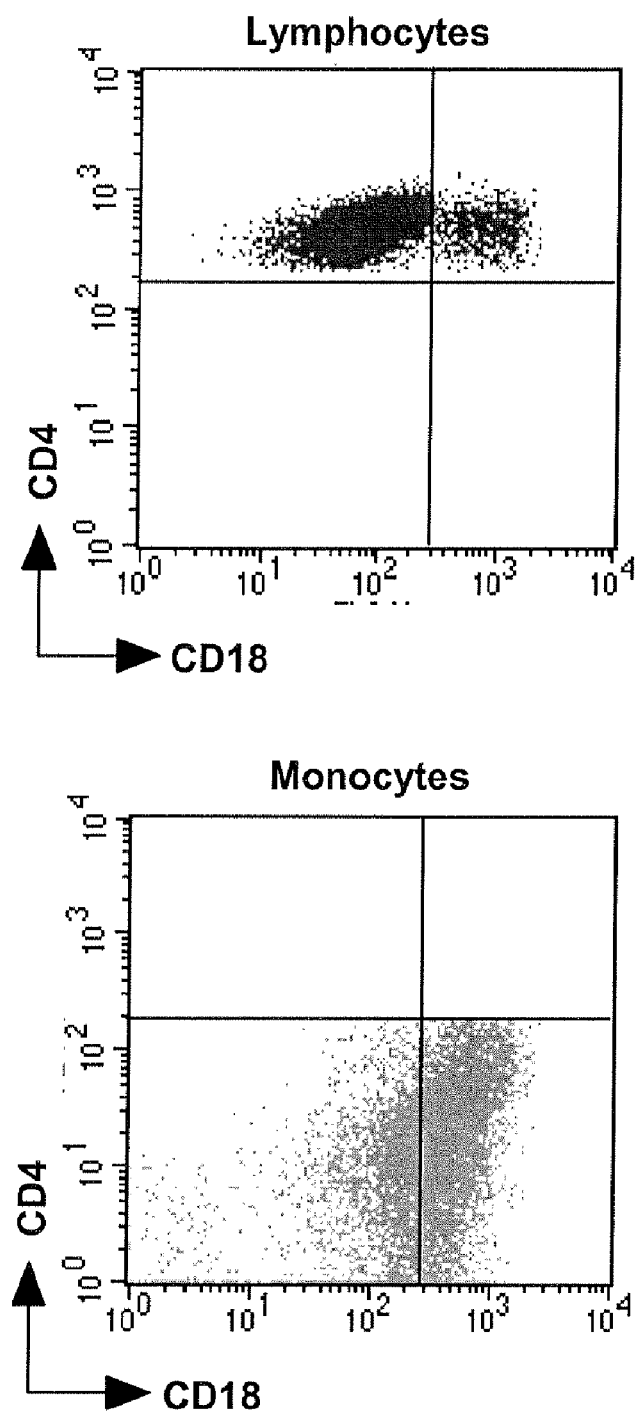

Thus, for example, by "CD3+ CD4+ CD18bright" phenotype for human T lymphocytes, we are referring to lymphocytes that express molecules or antigens CD3, CD4 and CD18 at the cell surface, wherein the fluorescence intensity of the marking of the CD18 molecule is equal to the fluorescence intensity of the same marking found on the monocyte cells (cf. FIG. 15).

The comparison of the expression by said lymphocytes of genes coding for the molecules of group B can be performed by comparing the amount of mRNA expressed for these genes.

Such a comparison of the expression of mRNA can be performed by using the polymerase chain amplification technique preceded by a reverse transcription step (RT-PCR).

According to an embodiment, the identification method according to the invention is characterized in that:
in step (a), the comparison of the expression by said lymphocytes of at least one gene encoding the molecules of group B is carried out by comparing the amount of mRNA expressed for said gene; and
in step (b), the lymphocytes that overexpress the mRNA of said gene are identified as Tr1-regulatory lymphocytes.

According to another embodiment, the identification method according to this invention is characterized in that the amount of mRNA is measured by quantitative RT-PCR.

According to another preferred embodiment, the identification method according to the invention is characterized in that the biological sample is obtained from a peripheral blood sample or from an inflammatory organ in a subject.

Preferably, in the method according to the invention, said biological sample is taken from a subject affected or likely to be affected by an autoimmune or inflammatory disease.

Still more preferably, said subject is affected by Crohn's disease or multiple sclerosis.

In another embodiment, the method for identifying Tr1 regulatory-lymphocytes according to the invention is characterized in that the biological sample is obtained from a method for in vitro preparation of Tr1-regulatory lymphocytes from a lymphocyte population obtained in a sample from a subject.

Said method for in vitro preparation of Tr1-regulatory lymphocytes from the lymphocyte population preferably includes at least one step in which CD4+ T lymphocytes of said lymphocyte population are activated in the presence of an antigen and interleukin 10.

In addition, said method for in vitro preparation of Tr1-regulatory lymphocytes comprises the following steps:
(a) obtaining a biological sample containing artificial antigen-presenting cells that express a molecule of the HLA class-II system and a human LFA-3 molecule and that do not express any co-stimulation molecules B7-1, B7-2, B7-H1, CD40, CD23 or ICAM-1;
(b) activating, in vitro, the CD4+T lymphocytes of said lymphocyte population in the presence of the selected antigen, presented by artificial antigen-presenting cells obtained in (a); and
(c) collecting, from said lymphocytes, an activated CD4+ lymphocyte population including at least 10% Tr1 lymphocytes specific to the selected antigen.

Said method for in vitro preparation of Tr1-regulatory lymphocytes also preferably comprises the following steps:
(a) obtaining, in vitro, a population of human progenitor cells capable of differentiating into dendritic cells;
(b) placing said human progenitor cells in a culture in the presence of IL-10 so as to obtain a population of said dendritic cells; and
(c) placing said human lymphocyte population in the presence of the dendritic cell population obtained in (b).

A preparation procedure of this type is provided as an example below (example 5).

In another embodiment, the identification method according to the invention is characterized in that the products for expression by said lymphocytes of genes encoding for the molecules of group A are mRNAs, and in that, in step (a), the determination of the simultaneous presence of said mRNAs is performed by RT-PCR.

An identification method according to the invention, in which the simultaneous presence of mRNAs is determined can be, for example, the polymerase chain amplification technique preceded by a reverse transcription step (RT-PCR).

According to another feature, the invention also relates to a method for quantifying Tr1-regulatory lymphocytes present in a biological sample including lymphocytes, characterized in that it comprises the steps of:
(a) identifying the Tr1-regulatory lymphocytes using an identification method according to the invention; and
(b) determining the proportion of Tr1-regulatory lymphocytes identified in (a) with respect to the total amount of lymphocytes or a particular fraction of lymphocytes, present in said biological sample.

Such a quantification method can be performed, for example, by means of flow cytometry as described above.

The invention also relates to a method for in vitro prognosis or diagnosis of an autoimmune or inflammatory disease in a subject, using a biological sample previously taken from said subject, characterized in that it comprises the following steps:
(a) determining the proportion of Tr1-regulatory-lymphocytes present in said biological sample with respect to the total amount of lymphocytes or a particular fraction of lymphocytes, according to the quantification method according to the method, or according to any method enabling said Tr1-regulatory lymphocytes to be quantified; and
(b) comparing the proportion of said Tr1-regulatory lymphocytes obtained in step (a) with that present in a biological sample taken from a healthy subject.

In the aforementioned prognostic or diagnostic method, in step (a), by any method enabling said Tr1-regulatory lymphocytes to be quantified, we are referring to a method in particular involving an evaluation of the proportion of lymphocytes having a cytokine production profile and/or capable of reducing the proliferation of CD4+ T cells as described in "Groux et al., 1997" and in the patent document published under the number WO 02/092793.

In a preferred embodiment, the method for in vitro prognosis or diagnosis of an autoimmune or inflammatory disease according to the invention is characterized in that, in step (b) of said method, a reduction of said proportion is observed in the subject to be tested.

Indeed, it has been possible to observe patients affected by an autoimmune or inflammatory disease showing a reduction in the proportion of Tr1-regulatory lymphocytes with respect to that present in a healthy subject, that is, a subject not affected by said disease.

The method for in vitro prognosis or diagnosis of an autoimmune or inflammatory disease has the major advantage of being fast and effective, and of being capable of being performed, for example, on a blood sample taken from a subject affected or likely to be affected with said disease. Thus, invasive methods or methods requiring hospitalization can be avoided.

The invention also relates to a method for enrichment of Tr1-regulatory lymphocytes present in a biological sample containing lymphocytes, characterized in that it comprises the following steps:
  (a) identifying the Tr1-regulatory lymphocytes using the identification method according to the invention; and
  (b) removing a significant portion of the lymphocytes not simultaneously having said molecules from said sample.

Among the methods that can be implemented in the enrichment method according to this invention, it is preferably to use a method implementing a cell sorter based on the simultaneous recognition of said molecules, in particular such as a flow cytometer capable of sorting and separating all cells simultaneously having the molecules of which the presence at the surface is to be determined.

Nevertheless, the enrichment method according to the invention can also be implemented in ways not involving flow cytometry. Indeed, the enrichment of Tr1 lymphocytes, in particular, for example, the Tr1 lymphocytes identified according to the identification method of the invention by the expression at their surface of molecules CD3, CD4, CD18 and CD49b (CD3+CD4+CD18brightCD49b+) from a lymphocyte population can be performed using magnetic beads in two steps: the first step will make it possible to deplete, from the total population, using magnetic beads adsorbed by an anti-mouse Ig antibody, the cells marked by anti-mouse CD8, CD14 and CD56 antibodies and the anti-human CD19 antibody. Indeed, the Tr1 cells do not express human molecules CD8, CD14, CD56 and CD19. The second step is a positive selection of cells expressing CD49b (CD49b+) by a marking of enriched cells by a mouse anti-human CD49b antibody and positive selection of cells marked by magnetic beads adsorbed by an anti-mouse Ig antibody. The magnetic bead cell separation and flow cytometry methods can be combined for the purification of Tr1 lymphocytes, for example those identified by the expression CD3+CD4+CD18brightCD49b+; for example, by a positive selection by magnetic beads of cells expressing CD4 (CD4+), then flow cytometric detection of molecules CD3, CD18 and CD49b, or positive selection of by magnetic beads of cells expressing (CD3+), then flow cytometric detection of molecules CD4, CD18 and CD49b, or positive selection by magnetic beads of cells expressing (CD49b+), then flow cytometric detection of molecules CD3, CD18 and CD49b. Such a procedure can also be applied to the detection of other molecules in the identification method according to the invention (CD11a, PSGL-1, PECAM-1, alphaV/beta3, and so on).

According to another feature, the invention relates to the use of a population of Tr1-regulatory lymphocytes enriched by an enrichment method according to the invention for the production of a drug intended to prevent and/or treat an autoimmune or inflammatory disease such as those cited above.

The use according to this invention is preferably characterized in that the Tr1-regulatory lymphocytes are administered at the level of an inflammation area.

In this application, the term inflammation or inflamed area refers to an area with an accumulation of fluids, plasma proteins, immune cells, substances such as proteins, which accumulation is due to a local injury, an infection, or a local immune injury. The inflammation can be episodic or chronic.

More preferably, the use according to this invention is characterized in that the Tr1-regulatory lymphocytes are administered with an antigen capable of activating said lymphocytes in vivo.

Thus, the Tr1-regulatory lymphocytes present at the level of the inflammation area can be activated in vivo by said antigen.

According to another embodiment, Tr1-regulatory lymphocytes that have previously been activated in vitro or in vivo are administered.

Finally, the invention also relates to a method for treating an autoimmune or inflammatory disease including the step of administering, to a patient, a population enriched with Tr1-regulatory lymphocytes by an enrichment method according to the invention.

The following legends of the figures and examples are intended to illustrate the invention without limiting its scope whatsoever.

LEGENDS OF THE FIGURES

FIG. 1: Characterization of CD4+CD18$^{bright}$ CD49b$^+$ T Cells Such as Mouse Tr1 Cells.

A) Analysis by FACS of the CD4+CD18$^{bright}$ CD49b$^+$ T cells using anti-CD4, anti-CD18 and anti-CD49b antibodies.

B) Cytokine production profile of CD4+CD18$^{bright}$ CD49b$^+$ T cells.

C) Measurement of the proliferation of CD4+ T cells cultivated alone (control) or in co-culture separated by a permeable membrane with CD4+CD18$^{bright}$ CD49b$^+$ or CD4+CD18int cells for 48 hours.

D) Study of the thickening of the ear after the epicutaneous application of hapten oxazolone in the mouse and after the injection of CD4+CD18$^{bright}$ CD49b$^+$ T cells and in mice treated with hapten but not injected.

E) Study of the proportion of CD4+ T lymphocytes in the colon in mice in which a chronic inflammation of the intestine has been induced, and injected or not with CD4+CD18$^{bright}$ CD49b$^+$ T cells.

Figure 2:
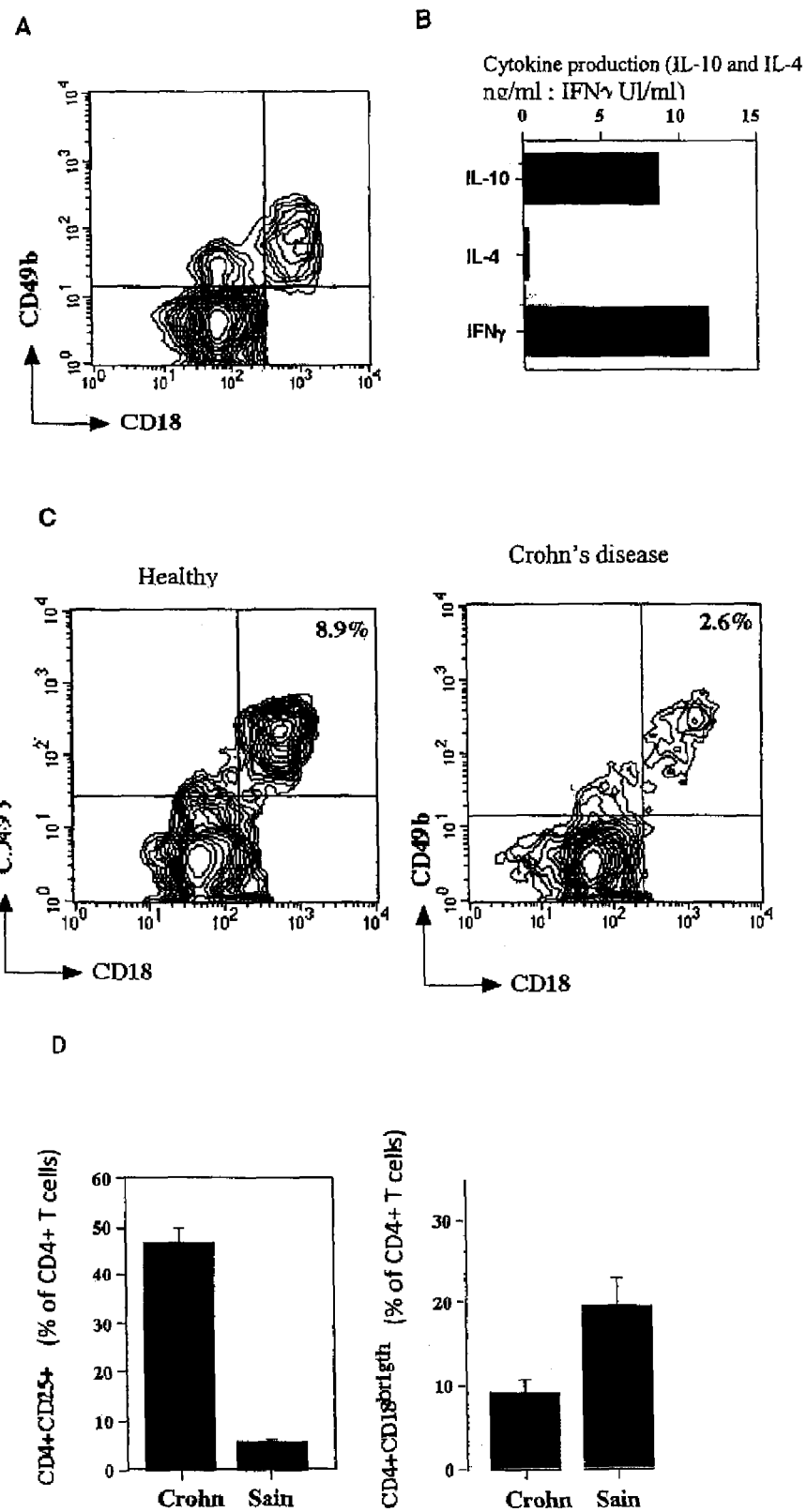

FIG. 2: Characterization of CD4+CD18$^{bright}$ CD49b$^+$ T Cells Such as Human Tr1 Cells.

A) Analysis by FACS of the CD3+CD4+CD18$^{bright}$CD49b$^+$ T cells using anti-CD3, anti-CD4, anti-CD18 and anti-CD49b antibodies.

B) Cytokine production profile of CD4+CD18$^{bright}$CD49b$^+$ T cells.

C) Comparative analysis by FACS of the CD3+CD4+CD18$^{bright}$CD49b$^+$ T cell populations present in the blood of healthy subjects and patients with Crohn's disease.

D) Comparative study by FACS of the CD3+CD4+CD18bright and CD4+CD25+ T cell populations present in the blood of healthy subjects and patients with Crohn's disease (analysis by flow cytometry).

Figure 3:
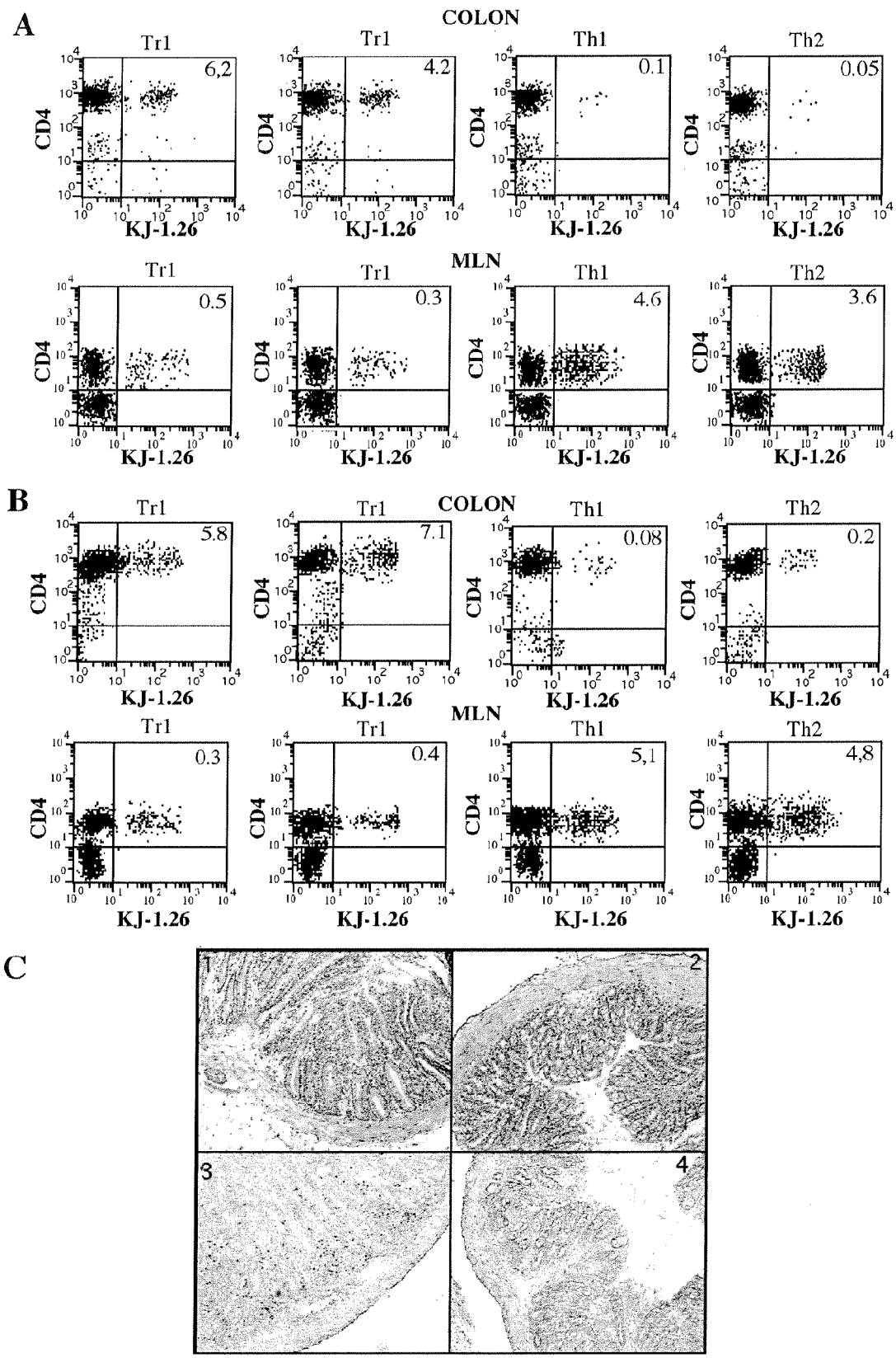

FIG. 3: The Tr1 Cells Preferably Migrate to the Inflamed Colon.

A-B) the CB-17 scid mice restored with CD4$^+$CD45Rb$^{hi}$ T cells were treated four weeks later with 5×10$^5$ clones of Tr1 T cells (Tr1 1:N10-7 and Tr1-2:A-10-9), Th1 (N12-8) and Th2 (N4-9) as shown. The mice were either fed with OVA in their drinking water (100 ng/ml) (A) or not fed with OVA (B). One week later, the mice were sacrificed and the cells present in the colon and the mesenteric lymph nodes (MLN) from each group of 5 mice were combined. The presence of CD4$^+$KJ-1,26$^+$ cells was analyzed by cytometry and the results indicated in the quadrants. The results show one representative experiment of four using Tr1 T cell populations Th1 or Th2, or T cell clones A-10-11, N-10-11, for Tr1 T cells N-12-4 and N-4-12, and for T cell clones Th1 and Th2, respectively.

C) the CB-17 scid mice were restored with CD4$^+$ CD45Rb$^{hi}$ T cells and treated with a Tr1 clone (Nice-2, 4×10$^5$ cells/mice) on day 0. One group of mice (1 and 3) was not fed with OVA while the other group of mice (2 and 4) was fed with OVA in its drinking water. Eight weeks later, the mice were sacrificed and their colons were examined by histology (groups 1 and 2). The presence of Tr1 cells was analyzed by immunohistochemistry using a biotinylated KJ-1,26 antibody (groups 3 and 4). High inflammation was detected in the colons of mice that were not fed with OVA (1, 3) while a specific activation of Tr1 clones inhibited the inflammation (2, 4). In spite of the absence of OVA, many KJ-1,26$^+$ cells were detected in the inflamed colons (group 3). Similar results were obtained in other experiments using the same or different Tr1 populations or clones.

Figure 4:
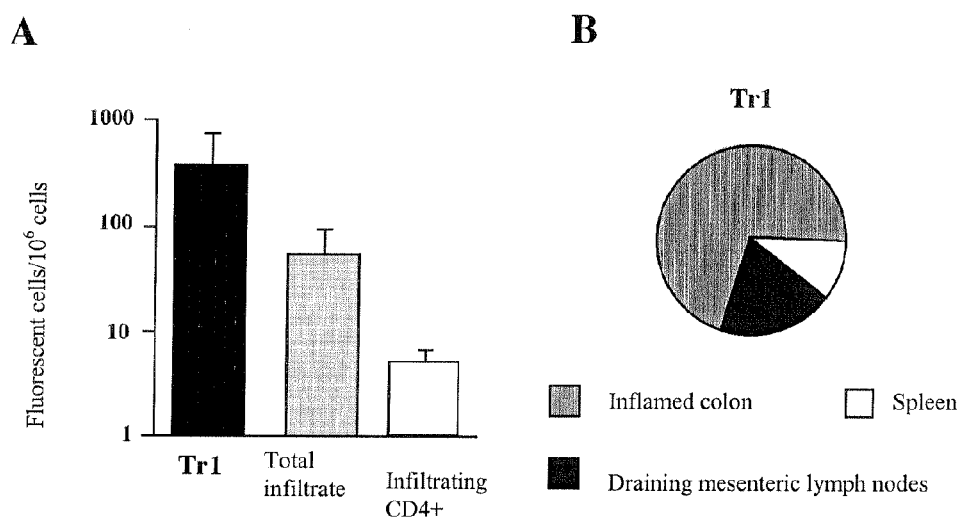

FIG. 4: The Migration of Tr1 Cells is Antigen-Dependent.

(A) The cells infiltrating the inflamed colon of CB-17 scid mice reconstituted with CD4$^+$CD45Rb$^{hi}$ T cells were collected four weeks after reconstitution. These cells containing a mixture of neutrophils, basophils and lymphocytes were marked with fluorescent calcein, AM. 10$^5$ of these fluorescent cells (gray bar) were co-injected intraperitoneally with 10$^6$ Tr1 cells (black bar) marked with orange CMTMR in the CB-17 scid mice reconstituted four weeks earlier with CD4$^+$CD45Rb$^{hi}$ T cells. Similar experiments were performed with CD4+ T cells isolated from a colon inflamed for 4 weeks (white bar). Twenty-four hours later, the cell content of the inflamed colon of the groups of two mice was examined by cytometry. Histograms show the absolute number of fluorescent cells collected per million total cells acquired. The results show one representative experiment of three.

B) The rates of absolute numbers of fluorescent Tr1 cells collected with respect to the total number of fluorescent cells collected are shown for each organ analyzed.

Figure 5:
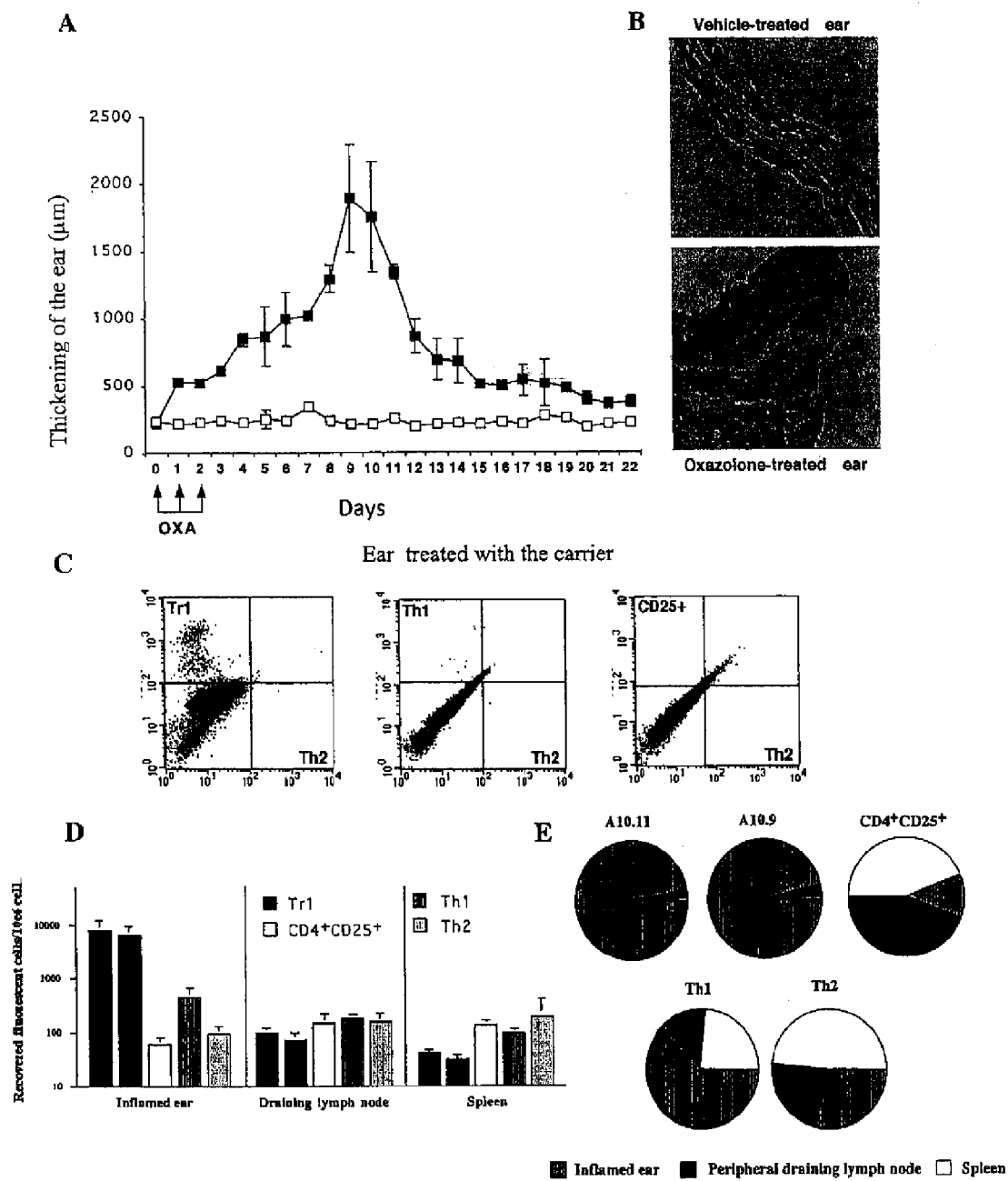

FIG. 5: The Tr1 Cells Migrate Toward Inflamed Ears.

A) Kinetics of contact sensitivity to oxazolone. BALB/c mice were treated with oxazolone (1 mg/ear) on day 0, 1 and 2. The swelling of the ear treated with oxazolone (black square) was compared with the ear treated with the control carrier for 22 days.

B) Histological analysis of oxazolone or ears treated with the carrier (magnification ×40) as shown.

C-E) The in vivo migration of cells Th1, Th2 and Tr1. The Tr1, Th1 and Th2 T cells were respectively marked with calcein blue, AM and orange CMTMR and co-injected into BALB/c mice treated 5 days earlier with oxazolone. Twenty-four hours later, the content of the fluorescent T lymphocytes of the ears treated with oxazolone, draining lymph nodes and spleen were analyzed by cytometry, as shown in C. The experiments were performed with a Tr1 clone (A-10-11, first black bars) or T cell populations Tr1 (second black bars), Th1 and Th2 as indicated (D)—Absolute numbers of Tr1, Th1 and Th2 cells measured in the inflamed ears, the draining lymph nodes and the spleen per 10$^6$ events acquired. The results shown are averages for groups of 4 to 10 mice (E)—The rates of absolute numbers of fluorescent Th1, Th2 or Tr1 cells with respect to the total number of fluorescent cells collected are shown for each organ analyzed.

Figure 6:
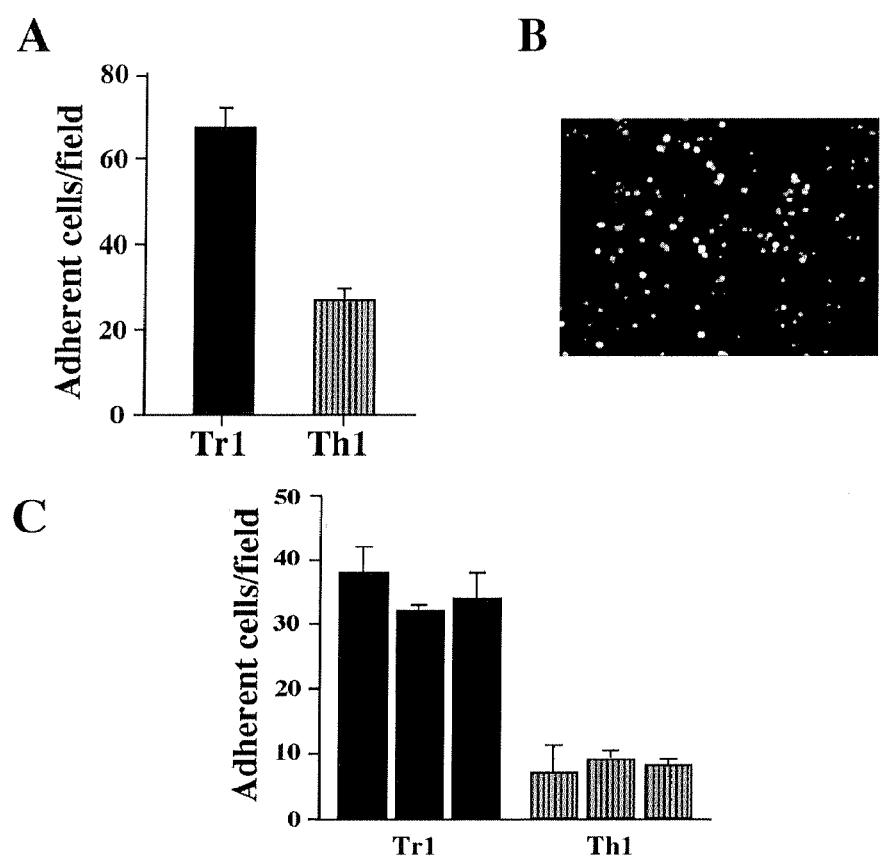

FIG. 6: The Tr1 Cells Showed Stopped More Frequently at Vascular Endothelial Cells Activated Under Flow Conditions.

A) Two different fluorescent dyes were used in this study: calcein, AM and orange CMTMR to marker Th1 and Tr1 cells. The cells were mixed in equal numbers and perfused through a flow chamber on a murine endothelial cell line activated by TNF-α, SVEC4-10 at a rate of 2 dyn/cm$^2$ for 15 min. The number of cells firmly stopped was quantified in 10 different fields. The results show the average±SD of five independent measurements for two clones and two populations in each group. The cells were marked indifferently with the different dyes and similar results were obtained.

B) Typical field showing Thr cells marked with green calcein and Tr1 cells marked with orange CMTMR firmly stopped on the murine endothelial cell line activated by TNF-α, SVEC4-10, magnification ×10.

C) For human T cell clones, a firm adhesion was analyzed on the murine endothelial cell line activated by TNF-α EA using the same experimental procedure as above. Several clones were used: JDV 15, BJF 308 and BJF 161 for Tr1 clones and JDV305, BJF180 and HAT203 for Th1 clones, respectively.

Figure 7:
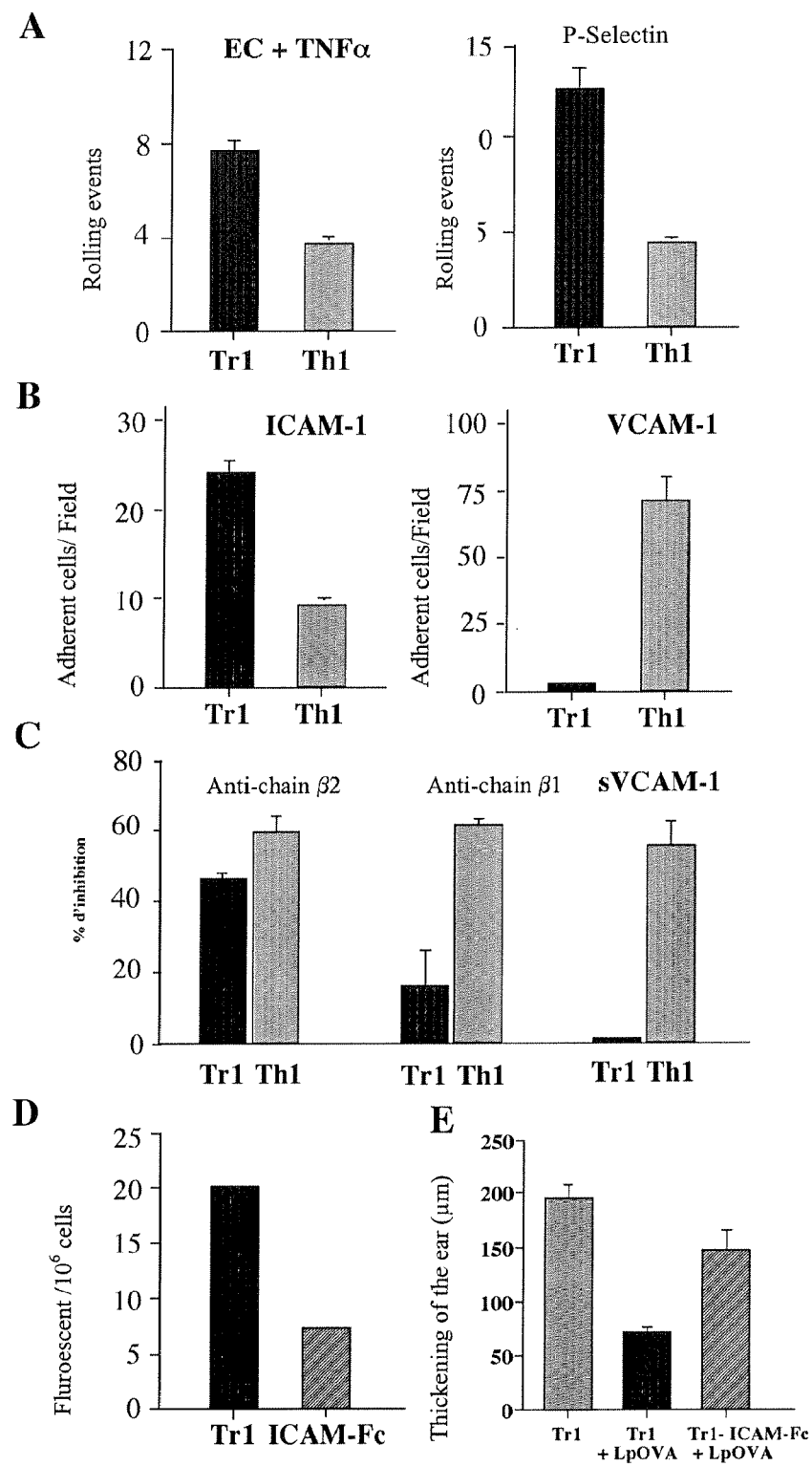

FIG. 7: Mechanisms for Greater Adhesion of Tr1 Cells to the Activated Endothelium.

The adhesion test on the flow chamber with a rate of 2 dyn/cm$^2$ was used to dissect the Tr1 adhesion mechanisms. Rolling and adhesion were compared for Th1 and Tr1 cells with calcein AM and orange CMTMR, respectively. The results show an average±SD of one representative experiment for two clones and two populations for each group.

A) The rolling events of Th1 and Tr1 cells on the endothelial cell line SVEC4-10 activated by TNF-α (EC) or on slides coated with the recombinant P-selectin molecule were counted after video recording of 9 different fields. One experiment of five.

B) The firm adhesion of Th1 and Tr1 cells was analyzed by flow on slides coated with recombinant mICAM-1 or mVCAM-1. One experiment of three.

C) Inhibitory effects of anti-β2, anti-β1 mAb integrin chains and the sVCAM-1 molecule on the firm stop of Tr1 and Th1 lymphocytes on SVEC4-10 activated by TNF-α was analyzed by flow. One experiment of five.

D) Migration inhibited by LFA-1 blocking Tr1 cells in inflamed ears. Tr1 cells were treated with ICAM-Fc (10 μg/ml) for 30 min at 4° C. and marked with calcein blue. The untreated Tr1 cells were marked with orange CMTMR. A mixture of Tr1 cells treated with untreated ICAM-1 Fe were co-injected into BALB/c mice sensitized 5 days earlier with oxazolone, as shown in FIG. 5. Twenty-four hours later, the content of the fluorescent T cells of the ears treated with oxazolone was analyzed by cytometry. The results show the absolute numbers of Tr1 cells measured in the inflamed ears per 10$^6$ events acquired. The results shown are taken from groups of 4 mice and were repeated with two different Tr1 clones (A10.11 and A10.9).

Figure 8:
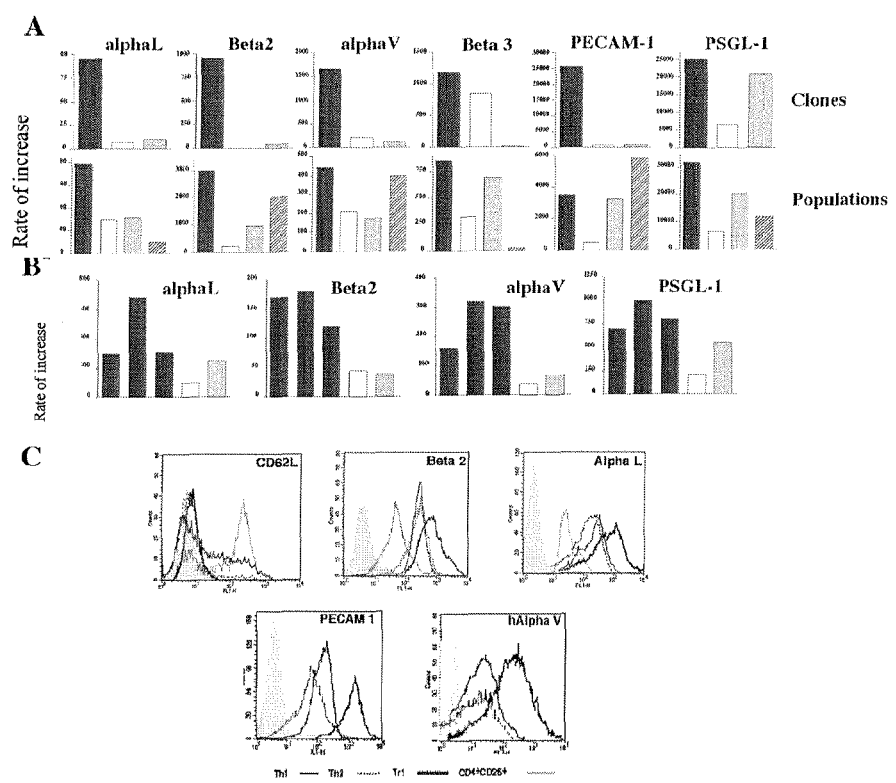

FIG. 8: Expression of Adhesion Molecules on Tr1 Cells.

A-B) Genetic expression levels of molecules alpha L, beta 2, alpha V, beta 3, PECAM-1 and PSGL-1 on clones and populations of human and mouse T cells Tr1 (gray bars), Th2 (white bars) and Th1 (black bars). For the mouse T cell clones, the results show an average of two of the three different clones analyzed. For the mice populations, two different populations were analyzed and the results show the average of the two values. For the human T cell clones, three different Tr1 clones and one Th1 and Th2 representative clone were analyzed. The values are expressed in rates of expression increase with respect to a negative control and show one experiment of three. Among the 45 different genes encoding the adhesion molecules tested for the human and mouse T cells, only those for which the difference between the Tr1 and Th1/Th2 cells was very high are shown.

C) FACS analysis of alphaL, beta2 and PECAM-1 integrin chains on a representative Tr1 mouse clone and alphaV integrin chain on a representative Tr1 human clone compared with representative Th1 and Th2 clones. One experiment of two.

Figure 9:
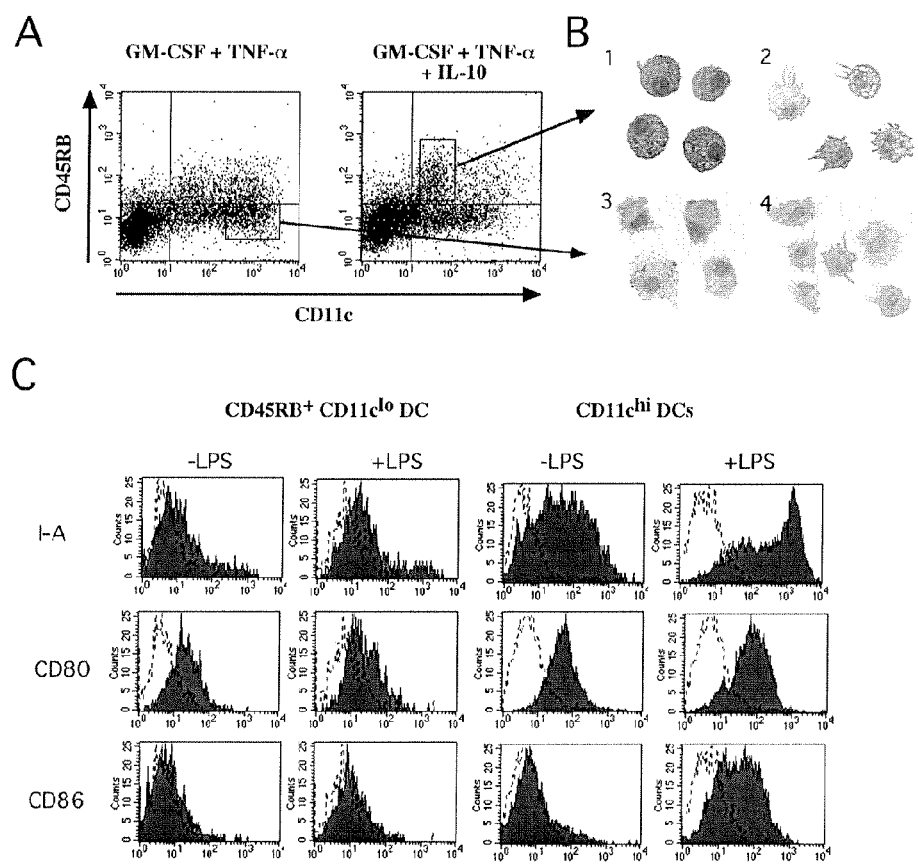

FIG. 9: IL-10 Induces Differentiation of Dendritic Cells $CD11c^{low}CD45RB^+$.

A) Bone marrow cells have been cultivated with GM-CSF and TNF-α in the presence or in the absence of IL-10 (50 or 500 ng/ml) as shown for 6 days, then activated for 24 h with LPS. The bone marrow dendritic cells thus generated were stained with a biotinylated anti-CD11c antibody, then with a streptavidin-peroxidase conjugate (PE). The cells were then conjugated to an anti-CD45RB antibody coupled to FITC and analyzed by flow cytometry. The data shows the results of one representative study of seven.

B) The dendritic cells were sorted according to the expression of CD11c and CD45RB, as shown in FIG. 11A. The sorted cells indicated were centrifuged and stained with May Gründwald Giemsa. 1—dendritic cells $CD11c^{low}CD45RB^+$ after 6 days of differentiation, 2—dendritic cells $CD11c^{low}CD45RB^+$ after activation by LPS, 3—dendritic cells $CD11c^{high}CD45RB^-$ after 6 days of differentiation, 4—dendritic cells $CD11c^{high}CD45RB^+$ after activation by LPS.

C) The dendritic cells obtained after in vitro differentiation in the presence of GM-CSF and TNF-α with or without IL-10, were sorted based on the expression of CD11c and CD45RB, as shown in FIG. 11A. The sorted cells were stained with antibodies marked with the FITC shown, and reanalyzed by FACS; they were also stimulated by LPS (1 µg/ml) for 24 h, stained with the ACm indicated and reanalyzed. The hatched histograms show the stained cells with control ACm of a corresponding isotype. The data shows the results of one representative experiment of three.

Figure 10:
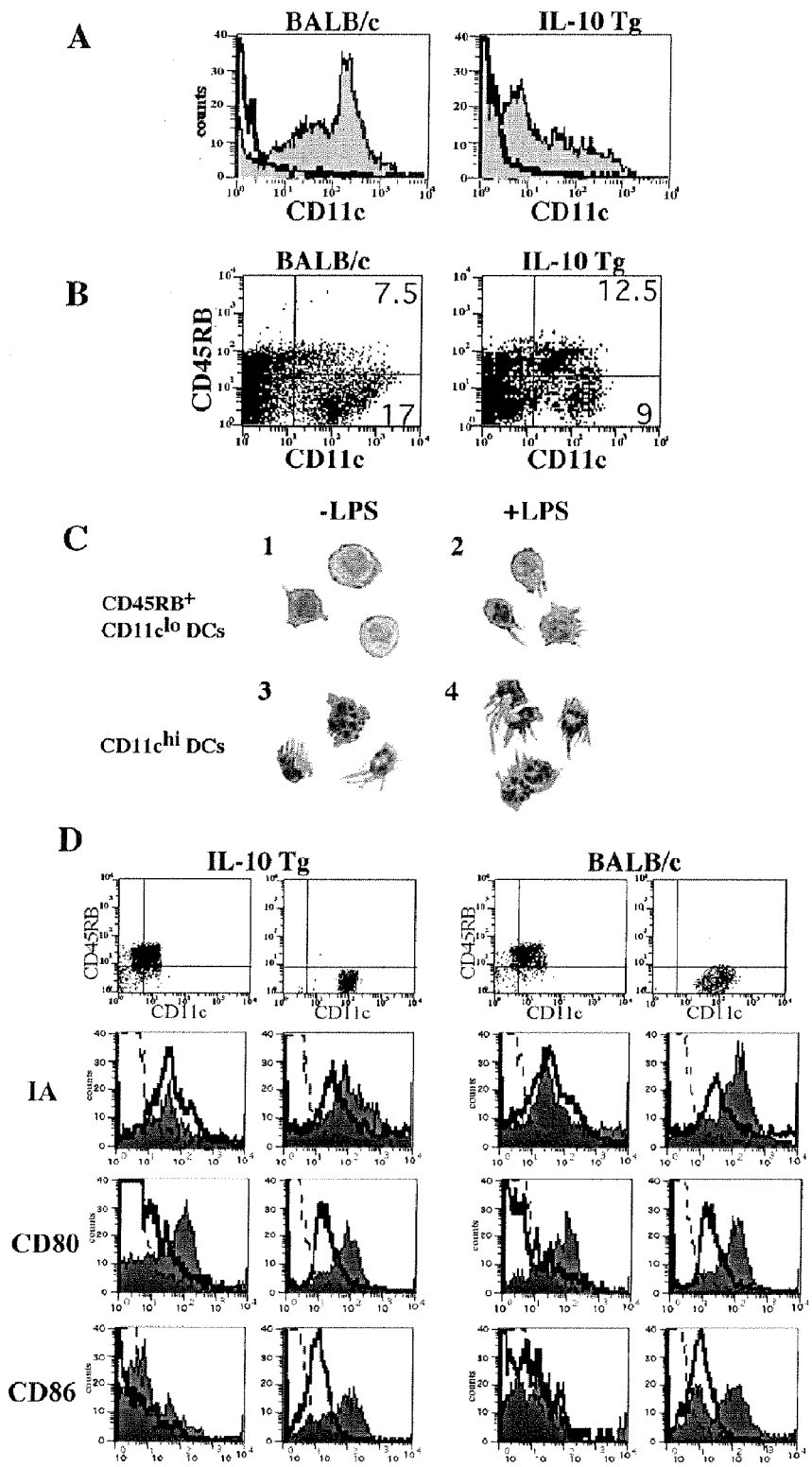

FIG. 10: Identification of Dendritic Cells Derived from IL-10 In Vivo.

A) Splenic dendritic cells (DC) of BALB/c or C57B1/6 IL-10, $IL-10^{-/-}$ and normal transgenic mice were isolated, enriched by cellular depletion with an antibody cocktail (ACm anti-B220, Gr1 and CD3), and the surface expression of the specific marker CD11 was analyzed by flow cytometry.

B) Preparations of DC enriched by cellular depletion with an antibody cocktail (ACm anti-B220, Gr1 and CD3) were isolated from the BALB/c or C57B1/6 IL-10, $IL-10^{-/-}$ and normal transgenic mouse spleen and analyzed for the expression of CD11c-cy5 and CD45RB-PE in order to distinguish two separate DC populations. The percentages in the different quadrants are indicated. The results of more than 10 experiments are typical. No difference was observed between the BALB/c non-transgenic mice and the controls was observed.

C) The sorted $CD11c^{low}CD45RB^+$ (1) and $CD11c^{high}CD45RB^-$ (3) cells isolated from the BALB/c mouse spleen were centrifuged and stained with May-Grünwald-Giemsa. The sorted $CD11c^{low}CD45RB^+$ (2) and $CD11c^{high}CD45RB^-$ (4) cells were also stimulated with LPS (1 µg/ml) in the presence of GM-CSF for 24 h, centrifuged and stained with May-Grünwald-Giemsa.

D) Enriched DC preparations from BALB/c or C57B1/6 IL10 Tg mice or controls were stained with CD11c-cy5 and CD45RB-PE. The cells were sorted with FACS on the basis of the expression of $CD11c^{low}CD45RB^+$ or $CD11c^{high}CD45RB^-$ and reanalyzed as shown. The sorted cells were then stained with the third marker coupled to the FITC and analyzed by cytofluorometry (empty histograms). The sorted DC were also stimulated with LPS (1 µg/ml) in the presence of GM-CSF for 24 h, stained with the ACm indicated and reanalyzed (full histograms). The hatched histograms show the control ACm of corresponding isotypes.

Figure 11:
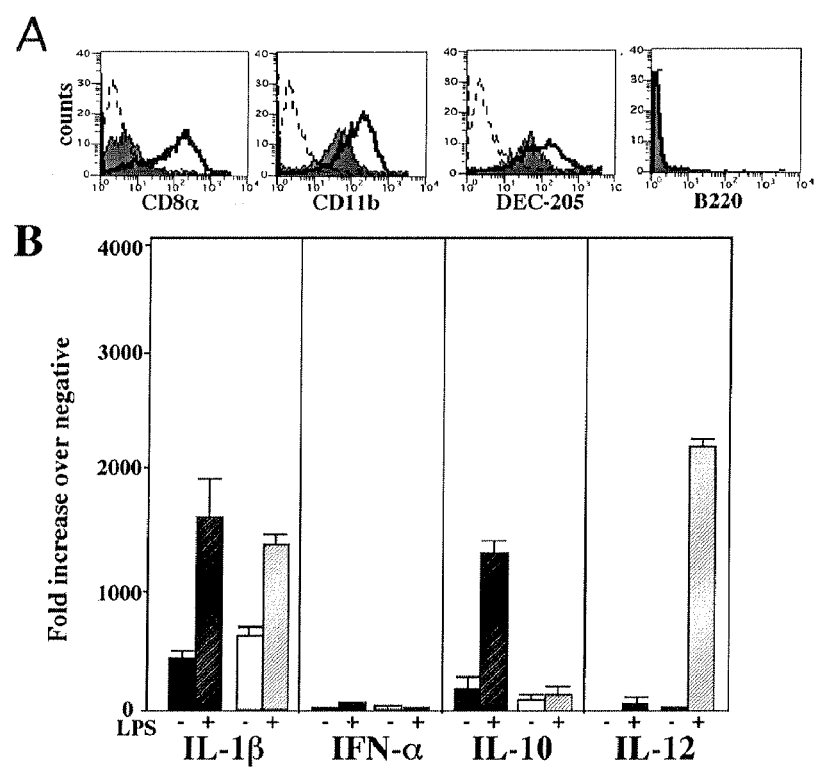

FIG. 11: Phenotypic Characterization and Secretion of Cytokines of the Subset of Dendritic Cells $CD11c^{low}CD45RB^+/B220^-$.

A) Enriched preparations of dendritic cells of BALB/c or C57B1/6 mice were stained with CD11c-cy5 and B220-PE and marked with antibodies coupled to FITC as shown. The cells were sorted on the basis of the expression of $CD11c^{low}CD45RB^+$ (full histograms) or $CD11c^{high}CD45RB^-$ (empty histograms, straight lines) and the stain for the third marker was analyzed for the various populations. The hatched histograms show the control ACm of a corresponding isotype.

B) Profile of cytokines of different sub-populations of dendritic cells.

Figure 12:
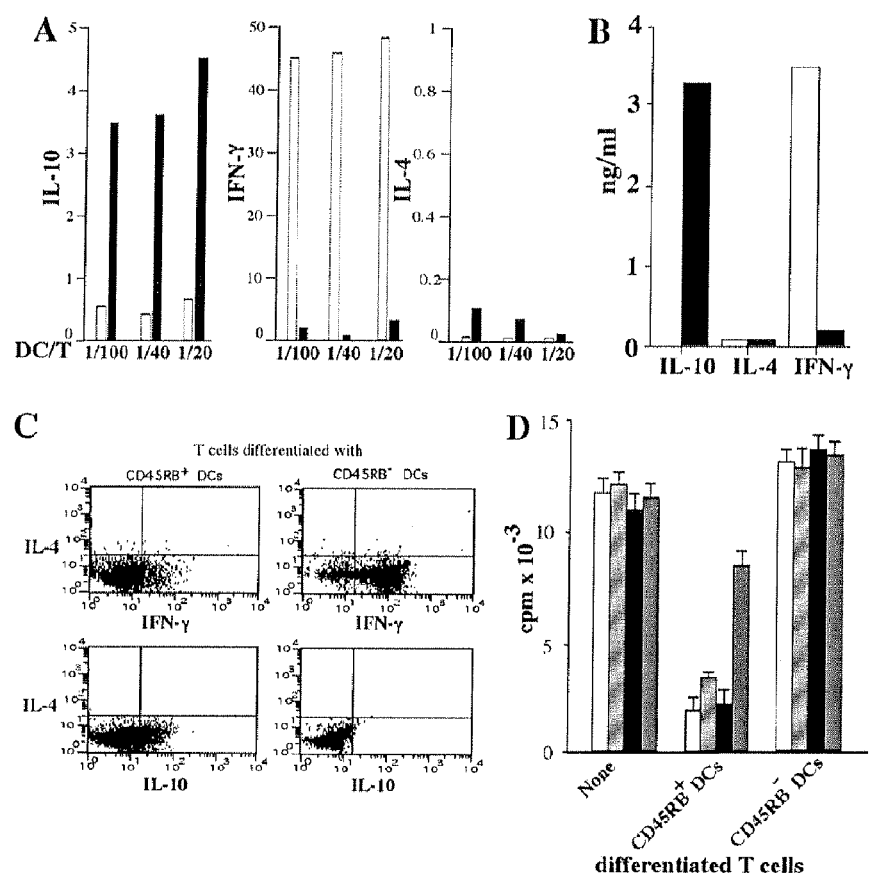

FIG. 12: The $CD11c^{low}CD45RB^+$ Dendritic Cells Induce the Differentiation of Tr1-Regulatory Cells In Vitro.

A) Analysis of cytokines secreted by populations of $CD4^+$ T cells activated with dendritic cells sorted ex vivo.

"Virgin" DO11-10 OVA TCR transgenic T cells were differentiated for 3 weeks with sorted DC $CD11c^{high}CD45RB^-$ (white bars) or $CD11c^{low}CD45RB^+$ (black bars), in the presence of OVA peptide. The dendritic cells were isolated from normal BALB/c mice with different DC/T ratios as indicated. After three weeks of culture, the T cells were harvested and stimulated with irradiated BALB/c splenocytes and OVA peptide (0.3 µM). Forty-eight hours later, the cytokines were analyzed by ELISA in the culture supernatants. The results show the average of 3 measurements and are expressed in ng/ml for IL-10 and IFN-γ and in pg/ml for IL-4. The data is representative of 5 distinct experiments with similar results.

B) Cytokines secreted by populations of $CD4^+$ T cells differentiated with dendritic cells derived in vitro.

Dendritic cells were obtained by culturing bone marrow cells in the presence of GM-CSF, TNF-α and IL-10. They were then sorted into two subsets: $CD11c^{high}CD45RB^-$ and $CD11c^{low}CD45RB^+$. The sorted dendritic cells were used to differentiate "virgin" CD4+ DO11-10 T cells, in a DC/T ratio of 1/20, in the presence of OVA peptide (0.6 µM). At the end of one week, the T cells were harvested and stimulated with irradiated splenic CPA and OVA peptide (0.3 µM). Forty-eight hours later, the cytokines were analyzed by ELISA in the culture supernatants. The results show the average of 3 measurements and are expressed in ng/ml. The data is representative of two distinct experiments with similar results.

C) Assay of intracellular cytokines of "virgin" DO11-10 T cells with OVA peptide and sorted $CD11c^{low}CD45RB^+$ or $CD11c^{high}CD45RB^-$ sorted DC.

$CD11c^{low}CD45RB^+$ and $CD11c^{high}CD45RB^-$ dendritic cells were isolated from normal BALB/c mice, sorted on FACS and placed in co-culture with "virgin" DO11-10 T cells in the presence of OVA peptide. Seven days later, the cells were harvested and stimulate for 6 h with cross-linked ACm anti-CD3 and CD28. Monensin was added for the last 4 hours of culture. The cells were then bound and stained for the assay of intracellular cytokines by specific ACm coupled to FITC or to PE, as indicated. One experiment of three is shown here.

D) Regulatory function of T cells differentiated with CD11c$^{low}$CD45RB$^+$ dendritic cells.

In the lower compartment of a transwell system, purified CD4+ T cells isolated from normal BALB/c mice were stimulated with irradiated BALB/c splenocytes and ACM anti-CD3 (white bars). In the upper compartment, CD4+ T cells differentiated by a single stimulation with CD11c$^{low}$CD45RB$^+$ or CD11c$^{high}$CD45RB$^-$ dendritic cells were stimulated by the OVA peptide and irradiated splenocytes. Co-culture experiments were also conducted in the presence of anti-IL-10 mouse ACm (10 µg/ml) (white hatched bars), anti-TGF-β mouse ACm (40 µg/ml) (black bars) or both (gray bars). Three days later, the slide tray was removed and the proliferative response of the spectator CD4+ T cells was measured after a pulse with 0.5 µCi of $^3$H-thymidine for the final 12 hours of the 72-hour culture. The results show the averages±SD of three measurements of one representative experiment of three.

Figure 13:
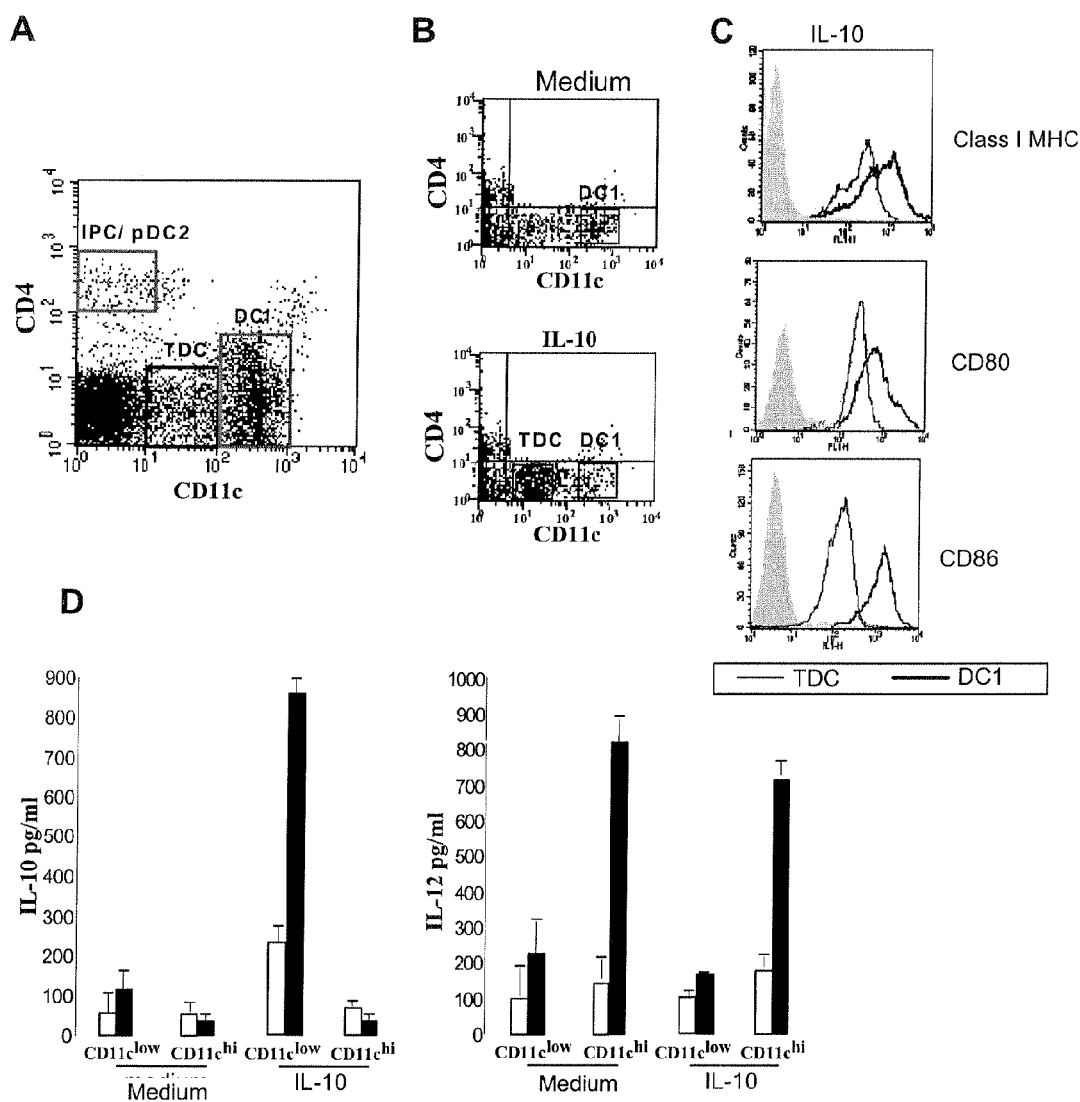

FIG. 13: Analysis of Human Tolerogenic Dendritic Cells (TDC).

A) the T and B cells of peripheral blood mononuclear cells were suppressed with antibodies and magnetic beads and the remaining population was analyzed for the expression of CD11c and CD4 by cytometry. The boxes show the two populations defined as DC1 and DC2 by "Siegal et al, 1999, Science, 281, 1835-7". A square shows the population of tolerogenic DC (TDC).

B) CD34+ progenitor cells were differentiated in vitro with GM-CSF (800 U/ml) and IL-4 (1000 U/ml) in the presence or in the absence of IL-10 (200 u/ml) as shown in example 8. The populations of TDC and DC1 were surrounded.

C) The TDC and DC1 cells were sorted by FACS according to the expression of CD11c and analyzed by cytofluorometry for the expression of HLA-DR, CD-80 and CD86. the results show that the TDC express lower levels of these molecules than the DC1 cells.

D) The TDC and DC1 cells were sorted by FACS according to, the expression of CD11c and stimulated by LPS for 24 h. The supernatants were then analyzed by ELISA for the presence of IL-10 and IL-12.

Figure 14:
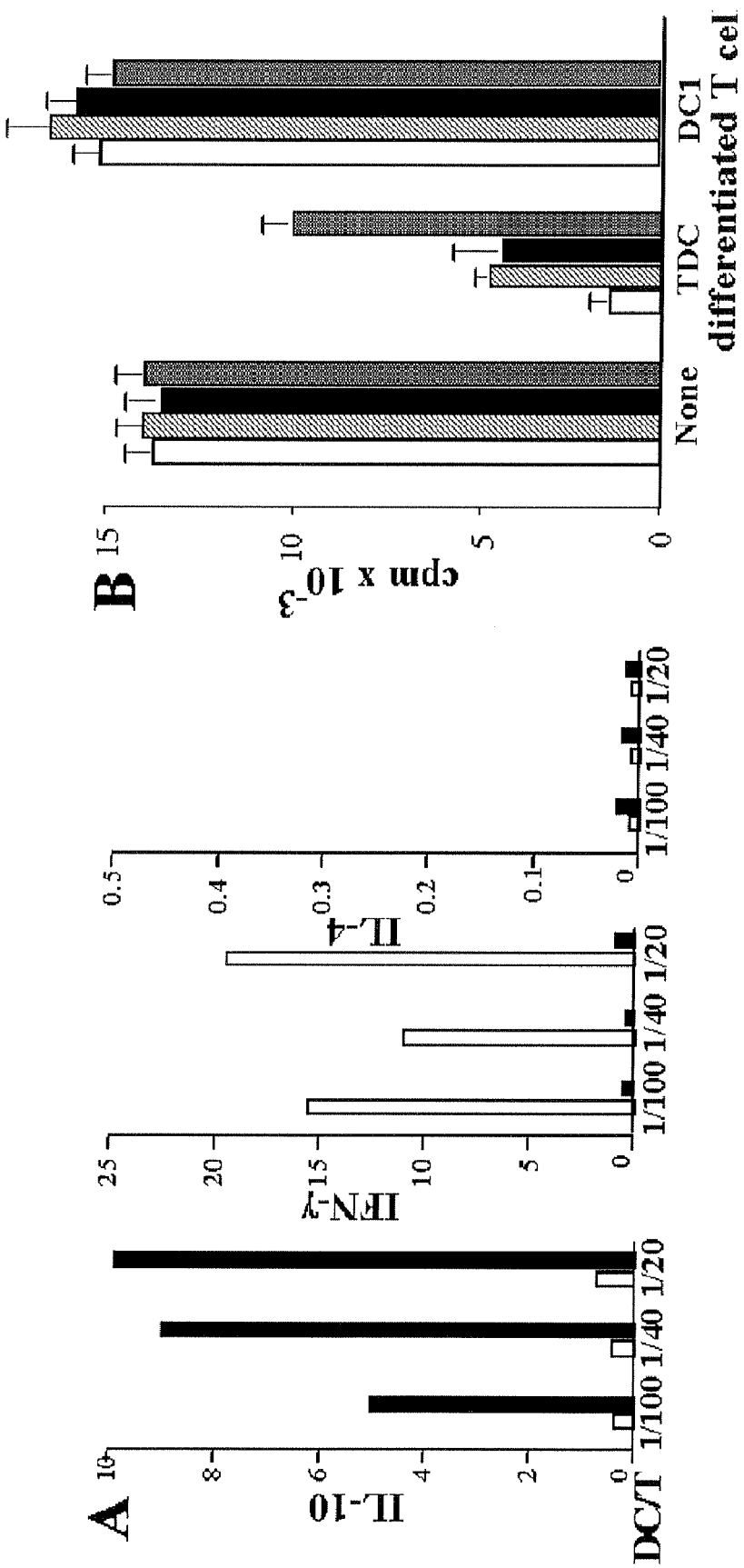

FIG. 14: TDC Inducing the Differentiation of Tr1 Cells Secreting High Levels of IL-10.

A) Analysis of cytokines secreted by the populations of CD4+ T cells activated with the sorted dendritic cells.

Human CD4+ T cells were stimulated for three weeks with sorted allogenic DC1 (white columns) or TDC (black columns) cells. The DCs using in vitro cultures in the presence (TDC) or in the absence (DC1) of IL-10 and used at different DC/T ratios as indicated. After the three-week culture, the T cells were harvested and stimulated with irradiated PBMC, and an anti-CD3 monoclonal antibody (10 µg/ml). After 48 hours, the cytokines in the culture supernatants were analyzed by ELISA. The results show the averages of three determinations and are expressed in ng/ml.

B) Regulatory Function of T Cells Differentiated with TDC.

In the lower compartment of a transwell system, purified human CD4+ T cells were stimulated by irradiated PBMC and an anti-CD3 monoclonal antibody (white columns). In the upper compartment, CD4+ T cells differentiated with allogenic TDC or DC1 cells as indicated were stimulated with irradiated allogenic PBMC. Co-culture experiments Were also implemented in the presence of monoclonal mouse antibodies blocking anti-IL-10 (10 µg/ml) (hatched columns), anti-TGF-β monoclonal antibodies (40 µg/ml) (black columns) or both (gray columns). After three days, the recipient was collected and the proliferative response of the CD4+ T cells was measured by adding 0.5 µCi of $^3$H-thymidine for the final 12 hours of the 72-hour culture.

FIG. 15: Definition of Human CD3+CD4+CD18Bright.

CD3+CD4+CD18bright cells are defined by the expression of CD3 and CD4 antigens at the cell surface and a fluorescence intensity of the CD18 marker found on the monocyte cells.

EXAMPLES

Example 1

Material and Methods

Material and Methods for Examples 2 and 3

Mice:

BALB/c and C.B-17 scid mice were obtained from CERJ (Le Genest Saint Isle, France). The DO11-10 homozygote mice came from a donation by Dr. S. D. Hurst (DNAX Research Institute, Palo Alto, Calif.). All of the mice are females aged 4 to 8 weeks at the beginning of each experiment.

Antibodies, Media and Reagents:

The medium used for the T cell cultures was the Yssel medium supplemented with 10% fetal bovine serum (Roche, Meylan, France) and $2 \times 10^{-5}$ M β2-mercaptoethanol (Invitrogen). The recombinant mouse IL-10 and IL-4 came from a donation by Dr. R. L. Coffman, DNAX Research Institute, Palo Alto, Calif. The recombinant mouse IFN-γ and IL-12 come from R&D Systems. The purified antibodies anti-IL-4 (11B11), anti-IL-10 (2A5), anti-IFN-γ (XGM1.2) and biotinylated antibodies anti-IL-4 (24G2), anti-IL-10 (SXC1) and anti-IFN-γ (R4-6A2) (Pharmingen Becton Dickinson) were used for the ELISA tests. The following monoclonal antibodies were used for the purification and phenotyping of mouse cells: anti-I-Ad (AMS-32.1), anti-CD8 (2-43), anti-CD11b (M1/70), anti-B220 (RA36B2), FITC-anti-CD45RB (16A), PC5-anti-CD4 (H129-19), PE-anti-CD18 (C71/16), FITC-anti-CD49b (Hal/29), FITC-anti-clonotype Kjl-26 and isotopic controls coupled to FITC- or PE (BD-Pharmingen, Le Pont de Claix, France). The antibodies directed against human surface molecules are: FITC- or PC5 anti-CD3 (UCHT-1) (Caltag), PC5- or APC-anti-CD4 (RPA-T4), PE-anti-CD18, and FITC-anti-CD49b (AK-7) (BD-Pharmingen). The OVA$_{323-339}$ peptide, Ovalbumin and Oxazolone come from Sigma (Saint Quentin Fallavier, France). The OVA$_{323-339}$ lipopeptide comes from Bachem (Voisin-le-Bretonneux, France).

Flow Cytometry and Cell Purification:

The CD4+ mouse cells were purified as described above (Groux et al, Nature, 1997). The splenocytes were depleted in cells B220$^+$, Mac-1$^+$, I-Ad$^+$ and CD8$^+$ by negative selection on magnetic beads adsorbed by sheep anti-rat Ig antibodies (Dynabeads, Dynal Biotech, Oslo, NO). The remaining cells were marked by antibodies FITC-anti-CD49b, PE-anti-CD18 and PC5-anti-CD4 and separated into CD4+CD18$^{bright}$CD49b$^+$ and CD4+CD18$^{int}$CD49b$^-$ by cell sorting on a FACStar SE (Becton Dickinson, France). The human CD4+CD18$^{bright}$CD49b$^+$ and CD4$^+$CD4+CD18$^{int}$CD49b$^-$ cells of the peripheral blood were sorted by after separation of the mononucleated cells by Ficoll gradient centrifugation, positive selection of the CD4$^+$ cells on anti-CD4 magnetic beads (Dynal Biotech) and marking of CD4+ cells with the PC5-anti-CD3, PE-anti-CD18 and FITC-anti-CD49b antibodies.

According to this protocol, the cell populations are more than 98% pure.

ELISA:

ELISA tests were used to measure human and mouse IL-4, IL-10 and IFN-γ. The cytokine concentrations were measured on the supernatants of Balb/c or human CD4+ CD18$^{bright}$CD49b$^+$ cells (2.10$^5$/well) activated for 48 h with an adsorbed anti-CD3 antibody (10 µg/ml) and a soluble anti-CD28 antibody (1 µg/ml).

Induction of Chronic Inflammatory Colitis:

Inflammatory colitis was induced by intraperitoneal injection in C.B-17 SCID mice of 2.10$^5$ CD4$^+$CD45RB$^{hi}$ T cells in 100 µl of PBS. A group of mice was treated with 1.10$^5$ CD4+CD18$^{bright}$CD49b+ T cells from DO11-10 mice. These mice were fed ovalbumin in their drinking water. Five weeks after the treatment, the mice were sacrificed and the proportion of TCD4+ cells in the colon was analyzed by flow cytometry, after digestion of the mucous membrane of the colon by collagenase/Dispase.

Delayed Hypersensitivity Reaction:

The delayed hypersensitivity reaction to oxazolone was induced by sensitization of the mice on day 0 by applying 25 ml of Oxazolone at 20 mg/ml to the skin of the abdomen. The delayed hypersensitivity reaction was then revealed on day 5, by 4 µl of Oxazolone at 4 mg/ml applied to each of the surfaces of an ear. Four hours later, 2.10$^5$ CD4+ CD18$^{bright}$CD49b$^+$ T cells were injected intravenously into the mice. Twenty µl of an OVA$_{323-339}$ lipopeptide solution at 500 µM diluted in olive oil was applied on days 4, 5 and 6 on the inflammatory ear. The thickening of the ear was measured once each day for 6 days.

Transwell Cell Cultures:

5.10$^5$ CD4+ T cells were deposited in a culture well in the presence of 4.10$^5$ irradiated splenocytes and a soluble anti-CD3 antibody (10 µg/ml). 2.10$^5$ CD4+CD18$^{bright}$CD49b$^+$ or CD4+CD18$^{int}$ T cells were activated in the same way and cultivated in a Transwell insert (pores of 0.4 µm) (Dutscher, Brumath, FR) deposited on wells containing CD4+ cells. The incorporation of tritiated thymidine with the target CD4+ cells was measured after 72 hours of culture.

Material and Methods for Example 4

Mice

BALC/c and C.B-17 scid mice free of any specific pathogen were obtained from CERJ (Le Genest Saint Isle, France). The mice were kept in our animal facility. The C.B-17 scid mice were housed in microisolators with sterile filtered air (Rec Biozone, Margate, UK). The female mice used were 8 to 12 weeks old.

Antibodies

The following monoclonal antibodies were used for the purification of mouse cells: AMS-32.1, anti-Iad, 2-43, anti-mouse CD8, MI/70, anti-mouse CD11b, RA36B2, anti-mouse B220, FITC-conjugated 16A, anti-mouse CD45RB, PE- or TC-conjugated GK1.5, anti-mouse CD4, biotinylated KJ-1,26 mAb or FITC revealed by PE-marked streptavidin, control antibodies of FITC- and PE-conjugated isotypes (BD-Pharmingen, Le Pont de Claix, France).

The antibodies directed against the adhesion molecules (BD-Pharmingen) were the following: alphaV integrin (23C6), alphaL integrin (M17/4), beta2 integrin (Game-46), beta1 integrin (HMβ1-1) and PECAM-1 (MEC 13.3). For the analysis of the expression of PECAM-1, alphaL integrin and beta2 integrin, the stain was revealed by FITC-coupled rabbit anti-rat immunoglobulins (Dako, Trappes, France).

Purification of Cells and Cytometry

Subsets of CD4$^+$ T cells were purified from mice spleens as described above (Groux et al, 1997). In short, the cells were reduced from B220$^+$, Mac-1$^+$, I-Ad$^+$ and CD8$^+$ cells by negative selection using Dynabeads coated with anti-ret in sheep (Dynal, Oslo, Norway). The remaining cells were marked by anti-CD45RB (25 µg/ml) conjugated with FITC, and anti-CD4 (10 µg/ml) conjugated with PE and separated into fractions of CD4$^+$CD45Rb$^{hi}$ and CD4$^+$CD45Rb$^{lo}$ sorted into two colors on the FACStar SE (Becton Dickinson, France). All of the populations were more than 98% pure after a new analysis. For the analysis of T cells infiltrating the colon, colon portions were stimulated and digested by collagenase (Life Technologies, Cergy Pontoise, France) for 2 h at 37° C. Cells were reduced from B220$^+$, Mac-1$^+$, I-Ad$^+$ and CD8$^+$ cells by negative selection using Dynabeads coated with anti-ret in sheep. The T cells were then analyzed by cytometry with an anti-CD4 and KJ-1,26 mAb Tricolor marked by FITC. For the analysis of mesenteric lymph nodes (MLN), combined mesenteric lymph nodes were stimulated and the cells were analyzed by cytometry with an anti-CD4 mAb marked by FITC and a biotinylated KJ-1,26 mAb revealed by PE streptavidin. For the migration studies, after digestion by collagenase, the CD4$^+$ cells of the colon were sorted using anti-CD4 conjugated with PE. To collect the lymphocytes of the inflamed cells, the ears were lightly immersed in PBS IX. Pieces of tissue were then washed once with PBS IX and digested for 30 minutes at 37° C. with Trypsin EDTA in Hank's Balanced Salt Solution (both of Life Technologies). The tissue treated with Trypsin were washed with 1 mg/ml of collagenase-dispase for 1 hour at 37° C. under constant agitation. The cell suspensions were washed in PBS IX and the supernatants containing lymphocytes were collected.

T Cells

The mouse T cell clones were obtained from DO11-10 mice after in vitro differentiation as described above (Groux et al, 1997). The naive KJ-1,26$^+$CD4$^+$ cells (MEL-14$^{hngnt}$) were repeatedly stimulated with OVA 323-339 peptide each week for 3 weeks, in the presence of IL-4 and anti-IL-12, IL-12 and anti-IL-4 or IL-10 for Th2, Th1 or Tr1 cells, respectively. Populations differentiated for three weeks were used in the study. To generate T cell clones, the different populations of T cells were cloned with one cell/well by cytometry (FACS vantage SE, Becton Dickinson) and stimulated by irradiated splenocytes (4500 rad) and OVA peptide. The clones were then dilated and analyzed for the secretion of cytokine after activation with the APCs and the OVA peptide. The selected clones were then stimulated with irradiated splenocytes and OVA peptide every two weeks and dilated a bit more with IL-2 (R&D System, Minneapolis, Minn. 10 ng/ml). The T cell clones were then used at least 10 days after the last stimulation.

The different human JDB T cell clones were described above (Groux et al, 1997) and obtained after MLR stimulation in the presence or absence of IL-10. The other T cell clones used were isolated from skin biopsies as described (Lecart et al, J Invest Dermatol. 2001 August; 117 (2): 318-25).

Cytokine Assays

Sandwich ELISA tests were used to assay the human and mouse IL-4, IL-10 and IFN-γ as described above (Groux et al, 1997).

Induction of Inflammatory Bowel Disease

IBD was induced in CB-17 scid mice with CD4$^+$CD45Rb$^{hi}$ T cells injected peritoneally in 100 µl of PBS. The inflammation was controlled by an injection of $2.10^5$ CD4$^+$CD45Rb$^{lo}$ T cells or different OVA-specific T cells as indicated.

Microscopic Colon Examination

Colons were removed from the mice and fixed in PBS containing 10% formaldehyde. Six mm cross-sections with paraffin inclusion were cut and stained with hematoxylin and eosin. The tissue were anonymously evaluated semi-quantitatively from 0 to 5. A 0 score was assigned when no change was observed. The changes typically associated with the other scores were as follows: score 1, dispersed infiltration of inflammatory cells of the mucous membrane, with or without minimal epithelial hyperplasia; score 2, benign inflammatory cell infiltration, diffusely dispersed, sometimes spreading into the mucous membrane and associated with erosions, with benign minimal epithelial hyperplasia and a benign minimal mucin depletion of the caliciform cells; score 3, benign-to-moderate inflammatory cell infiltration which was sometimes transmural, often associated with ulceration, with moderate epithelial hyperplasia and mucin depletion; score 4, significant inflammatory cell infiltration which was often transmural and associated with ulceration, with epithelial hyperplasia and significant mucin depletion; and score 5, significant transmural inflammation with acute ulceration and loss of intestinal glands.

Immunohistochemistry

Colon portions were frozen in liquid nitrogen and stored at −70° C. Five µm frozen cross-sections were cut and glued to glass slides. They were completely dried at room temperature for 1 hour and fixed in acetone at 4° C. for 15 min. Cross-sections were stained by an immunoenzymatic technique using a peroxidase-avidin-biotin system. In short, cross-sections were washed in PBS for 5 min. Then the cross-sections were saturated with biotin and avidin (Vector) according to the manufacturer's instructions and incubated with KJ-1,26 biotin or the control isotype. After being washed for 5 min in PBS, the cross-sections were incubated with peroxidase-streptavidin. After a final washing, the peroxidase was developed using the DAB vector staining kit (Vectastain, Vector), which gives a brown color.

Fluorescent Stains

Different stains were used in this study, from Molecular Probes (Molecular Probes, Eugene, Oreg., USA). Calcein blue is a fluorescent blue marker with excitation at 322 nm and emission at 435 nm; green-fluorescent fluorescein diacetate is a fluorescent green marker with excitation at 522 nm and emission at 529 nm, calcein AM is a fluorescent green marker with excitation at 494 nm and emission at 517 nm; orange fluorescent tetramethylrhodamine is a fluorescent red marker with excitation at 541 nm and emission at 567 nm. The T cells were marked in the medium with different probes (1 µg/ml) for 30 min at 37° C. in darkness and cleaned three times before use.

In Vitro Flow and Flow Chamber Studies

The endothelial cells of the transformed human umbilical vein EA hy926 was kindly provided by Dr. Edgell (University of North Carolina, Chapel Hill, N.C.) and cultured in DMEM (Life Technologies, Cergy Pontoise, France) supplemented by 20% FCS. The transformed murine endothelial cell line SVEC4-10 was purchased from ATCC and cultured with DMEM supplemented by 10% FCS. The flow chamber was purchased from Immuneties (Cambridge, Mass.). It was designed to allow for a stabilized laminar flow between 0.1 and 2 dyn/cm$^2$. The T cells at a concentration of $1 \times 10^6$ in HESS (Life Technologies) supplemented by 1 mM of CaCl$_2$ and MgCl$_2$ were perfused through the chamber on a monolayer of endothelial cells using a sampling syringe-pump (Harvard Apparatus, Boston, Mass.). In most of the experiments, the different T cell lines were marked with fluorescent stains, washed three times, then mixed and perfused on the murine endothelial cell line SVEC4-10 or the human EA cell line for 15 min. The medium was perfused in order to remove the lymphocytes that did not firmly adhere before quantification on 10 random fields of 0.65 mm$^2$ with objective 10×. For studies on inhibition, the soluble recombinant mVCAM-1, and the anti-beta1 and anti-beta2 integrin chains were used at 10 µg/ml and incubated with cells at +4° C., 30 minutes before the test. The recombinant mICAM-1 Fc chimeras, the recombinant mVCAM-1 Fc chimeras and the recombinant chimeras in selectin mP Fe were coated with 2 µg/ml (R&D systems). For the rolling studies, the perfused cells were monitored by video recording and the mobile cells were counted on 9 distinct fields for each subset of fluorescent T cells.

In Vivo Migration Tests

The T lymphocytes were first marked with fluorescent stains. The Th1, Th2 and Tr1 cells were incubated at a concentration of $2.10^6$ cells/ml in PBS IX and marked with µg/ml of calcein, AM; 2 µg/ml of orange CMTMR or 2 µg/ml of calcein blue, for 30 minutes at 37° C. The cells were then washed twice in PBS IX (Life Technologies). The fluorescent cell suspensions were mixed. The mice received 100 µl of PBS IX containing 1 million of each cell population intravenously. Twenty-four hours after the cell transfer, the distribution of fluorescent cell tissue was analyzed by cytometry on a FACS SE apparatus (Becton Dickinson, Le Pont de Claix, France). To specifically analyze the T cells injected, the FACS acquisition was performed on a gate defined for SSC-FSC parameters (SSC for side light scatter; and FSC for forward light scatter) of mixed fluorescent cells taken before the cell transfer. The number of Th1, Th2 or Tr1 in each organ was evaluated for a total of $10^6$ cells acquired. For the blocking of the LFA-1, the ICAM 1Fc chimera (R&D Systems) was used at 10 µg/ml for 30 min at +4° C., before the cell injection.

Oxazolone Contact Sensitivity

The oxazolone contact sensitivity (Sigma, L'Isle d'Abeau, France) was performed by applying 20 µl of an oxazolone solution of 50 mg/ml in olive oil/acetone (4:1, vol:vol) epicutaneously on the right ear once per day for three days. The left ear received only the carrier. The thickness of the ear was checked each day.

In Vitro Chemotaxis

Before migration, the Th1 and Th2 cells were first marked with calcein, AM and orange CMTMR as described above. The Tr1 cells remained unmarked. $10^5$ cells of each population in 150 µl of heated RPMI, 20 mM Hepes, 1% FCS (all of Life Technologies) were applied in an insert between wells with 5-µm pores (Corning Costar, Brumath, France). Only 600 µl of migration medium or SDF-1/CXCL12 (Prepotech, Rocky Hill, N.J.), Mig/CXCL9 or SLC/CCL21 (R&D Systems) were distributed in the lower chamber, next to the insert between wells. After 3 hours at 37° C., the cells that had migrated toward the lower chamber were harvested and the differential migration of each cell population was analyzed by cytometry.

Real-Time Quantitative RT-PCR Test

The total RNA was prepared by using TRIZOL (Life Technologies) and any potential contaminating chromosomal DNA was digested by DNase 1 according to the manufacturer's instructions (Gene Hunter, Nashville, Tex.). Then, the RNA was reverse transcribed using obligo(dT)12-18 and the Superscript II reverse transcriptase (Life Technologies). The real-time quantitative PCR was performed with the kit of green PCR SYBR reagents in special microtitration plates with 96 optical wells (Applied Biosystems, Courtaboeuf, France) in an ABI PRISM 5700 sequence detection system (Applied Biosystems), according to the manufacturer's instructions. Fluorescence signals were generated during each PCR cycle by direct incorporation of green double strand SYBR DNA so as to provide quantitative PCR information in real time. The primers (MWG Biotech, Ebersbert, Germany) were designed to measure the exon-intron junctions so as to prevent genomic DNA amplification and to obtain amplimers between 100 and 150 by so as to increase the efficiency of the PCR amplification. All of the primers were used under conditions that prevented the formation of dimers and the accuracy of the amplified products was tested by electrophoresis and the restriction enzyme digestion maps. All of the cDNA were assayed on the value of the average expression of 4 different domestic genes. The PCR conditions were 10 min at 94° C., 40 cycles of 30 s at 94° C., 30 s at 60° C. and 30 s at 72° C. for each amplification in a final volume of 20 µl. The target gene expression was measured after normalization of the RNA concentrations with 4 different domestic genes and the values are expressed in terms of increased expression over a negative control.

Example 2

Characterization of CD4+CD18$^{bright}$CD49b$^+$ T Cells Such as Mouse Tr1 Cells FACS Analysis of CD4+CD18$^{bright}$CD49b$^+$ T Cells from a Biological Sample of Murine Splenocytes.

BALB/c mouse splenocytes were marked with FITC-conjugated anti-CD3 antibodies, PC5-conjugated anti-CD4 antibodies and PE-conjugated CD18 antibodies. The FACS analysis of CD3$^+$CD4$^+$ T cells shows the presence of a population capable of overexpressing the CD18 antigen and the represents 14% of all the CD4$^+$ T cells (FIG. 1A). BALB/c mouse splenocytes were marked with PC5-conjugated anti-CD4 antibodies, PE-conjugated CD18 antibodies and FITC-conjugated anti-CD49 antibodies. The FACS analysis of the CD4$^+$ T cells shows that 35% of the CD18$^{bright}$CD4$^+$ T cells in the mouse also overexpress the CD49b antigen (FIG. 1B).

Profile of Cytokine Production by CD4$^+$CD18$^{bright}$CD49b$^+$ T Cells

CD4$^+$CD18$^{bright}$CD49b$^+$ T cells were sorted by the FACS technique after CD4, CD18 and CD49b detection of BALB/c mouse splenocytes. The CD4$^+$CD18$^{bright}$CD49b$^+$ T cells were then activated in vitro using marked anti-CD3 antibodies (10 µg/ml) and soluble anti-CD28 antibodies (1 µg/ml). The supernatants were collected after 48 hours of culture and an ELISA test was performed to determine the presence of IL-10, IL-4, IFNγ. The results show that the CD4$^+$CD18$^{bright}$CD49b$^+$ T cells have the same cytokine production profile as those described for Tr1 T lymphocytes (large production of IL-10, production of IFNγ and absence of IL-4 production) (FIG. 1C).

Proliferative Study of CD4+ T Cells by Incorporation of $^3$H-Thymidine.

The sorted CD4$^+$CD18$^{bright}$CD49b$^+$ or D4$^+$CD18$^{bright}$CD49b$^-$ T cells and the CD4$^+$ cells are cultured in the presence of irradiated splenocytes and soluble anti-CD3 antibodies (10 µg/ml). The two cell populations were separated by a polycarbonate membrane (pores of 0.4 µm). After three days of culture, the proliferation of the total CD4$^+$ T cell population was measured by incorporation of $^3$H-thymidine. These experiments show that the CD4$^+$CD18$^{bright}$CD49b$^+$ T cells are capable of inhibiting the proliferation of bystander CD4$^+$ T cells according to a mechanism depending on soluble factors, a mechanism specific to Tr1 cells (FIG. 1D).

Injection of CD4$^+$CD18$^{bright}$CD49b$^+$ T Cells in Mice Having an Inflammation of the Ear.

The delayed skin hypersensitivity to hapten oxazolone was induced in BALB/c mice by an epicutaneous application of hapten. The mice treated with oxazolone were injected with sorted CD4$^+$CD18$^{bright}$CD49b$^+$ T cells from DO11-10 transgenic mice for an anti-ovalbumin TCR (T-Cell Receptor). The mice were then treated or not with the ovalbumin lipopeptide in the inflamed ear so as to activate specifically the injected cells. The swelling of the ear was measured over time, starting with the cell injection, for four days. The results show that the CD4$^+$CD18$^{bright}$CD49b$^+$ T cells are capable of inhibiting, in vivo, the cutaneous inflammation only when they are activated with the ovalbumin lipopeptide. These results correspond to the in vivo inhibiting effect of Tr1 T cell clones in the same pathogenic model (FIG. 1E).

Proliferative Study of CD4$^+$ T Cells in Mice with Bowel Disease after Injection of CD4$^+$CD18$^{Bright}$CD49b$^+$ T Cells.

SCID mice were injected with CD4$^+$CD45RB$^{high}$ to induce inflammatory bowel disease. One group of mice was also treated with sorted CD4$^+$CD18$^{bright}$CD49b$^+$ T cells from DO11-10 transgenic mice and fed ovalbumin. Eight days after the cell injection, the proportion of CD4$^+$ T cells in the mucous membrane of the colon was analyzed by flow cytometry. While the control mice have a severe bowel inflammation and a high proportion of CD4$^+$ T cells inside the cellular infiltrate, the mice treated with CD4$^+$CD18$^{bright}$CD49b$^+$ T cells are protected from inflammation and have a small infiltration of CD4$^+$ T cells in the colon. These experiments show that, as Tr1 T cells, the CD4$^+$CD18$^{bright}$CD49b$^+$ T cells are capable of protecting mice from inflammatory bowel disease (FIG. 1F).

Example 3

Characterization of Human CD4$^+$CD18$^{bright}$CD49b$^+$ T Cells

FACS Analysis of CD4$^+$CD18$^{bright}$CD49b$^+$ T Cells from a Biological Sample of PBMC Cells.

Peripheral blood mononuclear cells were separated by centrifugation in a Ficoll gradient and were marked with APC-conjugated anti-CD4 antibodies, PC5-conjugated anti-CD3 antibodies, PE-conjugated anti-CD18 antibodies and FITC-conjugated anti-CD49b antibodies. The FACS analysis of CD3$^+$CD4$^+$ T cells shows the presence of a population capable of overexpressing the CD18 antigen and representing 20% of CD3$^+$CD4$^+$ T cells in human blood (FIG. 2A). The FACS analysis of CD3$^+$CD4$^+$ T cells shows that the CD18$^{bright}$CD4$^+$ T cells in human blood also overexpress the CD49b antigen (FIG. 2B).

Profile of Cytokine Production by CD4$^+$CD18$^{Bright}$CD49b$^+$ T Cells.

Human CD4$^+$CD18$^{bright}$ T cells were separated by cell sorting according to the FACS technique after CD4 and CD18 marking of mononuclear blood cells. The $CD4^+CD18^{bright}$ T cells were then activated in vitro with the antibody marked anti-CD3 (10 µg/ml) and soluble anti-CD28 antibodies (1 µg/ml). The supernatants were collected after 48 hours of culture and an ELISA test was performed in order to detect the presence of IL-10 and IL-4 and IFN-γ. The results show that the human $CD4^+CD18^{bright}$ T cells, like their murine homologues, have the same cytokine production profile as described for Tr1 T lymphocytes (large production of IL-10, production of IFNγ and absence of IL-4 production) (FIG. 2C). Comparative FACS analysis of $CD4^+CD18^{bright}CD49b^+$ T cells present in healthy subjects and in patients with Crohn's disease.

The proportion of $CD4^+CD18^{bright}$ $CD49b^+$ T cells in the blood was compared between healthy subjects and patients with Crohn's disease. The analysis of the $CD3^+CD4^+$ T cells shows, with respect to a subject representative of each group, that the proportion of $CD4^+CD18^{bright}$ $CD49b^+$ T cells is reduced in patients with Crohn's disease (FIG. 2D).

The proportion of $CD4^+CD18^{bright}$ T cells in healthy subjects and in patients with Crohn's disease is inversely correlated with that of the activated $CD25^+$ $CD4^+$ T cells, as shown by the flow cytometry. The patients with Crohn's disease (n=4) show an increase in the number of $CD25^+$ $CD4^+$ blood T cells and a reduction in the number of $CD4^+CD18^{bright}$ T cells compared with the healthy subjects (n=5) (FIG. 2E).

Example 4

The Overexpression of a Set of Adhesion Molecules on Tr1-Regulatory Lymphocytes Allows for their Specific Migration to Inflamed Tissue There is now incontestable proof of a subpopulation of $CD4^+$ regulatory T cells which, in vivo, modulate harmful immunopathological responses. These cells have potential therapeutic advantages for treating autoimmune disease, but many primary aspects of their regulatory mechanisms are still overlooked, in particular with regard to their migratory behavior, their exact site of action and the molecular pathways involved in these mechanisms. In two different inflammation models, diagrams of the migration of Tr1 cells were compared with those of Th1 and Th2 effector cells obtained after in vitro differentiation. It was shown that the Tr1 cells preferably migrate toward inflamed tissue and very little toward secondary immune organs, unlike Th1 and Th2 cells. The analysis of all of the chemokin receptors known did not reveal any specific expression that might explain the migration specific to Tr1 cells. However, under flow conditions, human or mouse Tr1 cells show greater stopping at the inflammatory vascular endothelium. The analysis of adhesion molecules revealed a molecular design specific to Tr1 cells with increased regulated function and expression of PSGL-1, LFA-1, alphaV/beta3 and PECAM-1. These results show that Tr1 cells represent a subset of regulatory T cells that are specialized in the control of inflammatory sites.

Tr1 Cells Preferably Migrate to the Inflamed Colon.

In previous experiment, the inventors showed that the Tr1 cells could prevent inflammation in a model of inflammatory bowel disease (IBD) caused experimentally in scid mice (Groux et al, 1997; Immunol Today. 1999 October; 20 (10): 442-5). To determine the site of action of Tr1 cells in vivo in the control of IBD, CB-17 scid mice were reconstituted with pathogenic $CD4^+CD45Rb^{hi}$ $T^+$ cells to cause IBD. Four weeks after the transfer, they were injected intravenously with different specific cells OVA Th1, Th2 and Tr1 ($2\times10^6$ cells) and were fed OVA in their drinking water, a situation in which a complete inhibition of colitis was observed with the Tr1 cells. One week later, the mice were sacrificed and the presence of $KJ-1,26^+$ cells (OVA-specific T cells) was analyzed in the colon, the spleen and the mesenteric lymph nodes. Many $KJ-1,26^+$ cells were observed in inflamed colons of mice treated with Tr1 cells (FIG. 3A). By contrast, in mice treated with OVA-specific Th1 and Th2 cells, fewer $CD4^+KJ-1,26^+$ T cells were detected among the cells that infiltrated into the colon. The analysis of draining mesenteric lymph nodes and spleens (not shown) revealed an accumulation of Th1 or Th2 cells while only a few Tr1 cells were observed (FIG. 3A). Similar results were observed when the different T cells were injected on day 0 at the same time as pathogenic $CD4^+CD45RB^{hi}$ T cells (not shown). The inventors and others (Groux et al, 1997; Barrat et al, J Exp Med 2002 Mar. 4; 195 (5): 603-16) showed in two different inflammation models that the specific antigen (ovalbumin) must be injected locally (orally) in the IBD model (Groux et al, 1997) or intracranially in the EAE model (Barrat et al, 2002) to introduce the protective effect of Tr1 cells, and that the systemic injection of the antigen (iv or ip injection) was ineffective. These results suggested that the local activation of Tr1 cells was necessary. The inventors therefore performed analyses to see whether the presence of the antigen at the inflammation site was also required for the migration of Tr1 cells into the inflamed colon. CB17 scid mice received injections of $CD4^+$ $CD45RB^{hi}$ T cells and OVA-specific Tr1 cells simultaneously (FIG. 3C) or four weeks after reconstitution (FIG. 3B), in the presence or the absence of OVA. The analysis of $KJ1-26^+$ Tr1 cells injected by immunochemistry (FIG. 3C) or by flow cytometry (FIG. 3B) showed that the Tr1 cells migrate specifically toward the inflamed colon even in the absence of their specific antigen. However, the activation of the antigen specific to Tr1 cells was necessary to activate their regulatory function as shown by the infiltration of the leukocytes and the inflammation observed in the mice that were not treated with ovalbumin, in spite of the presence of infiltrated Tr1 cells (FIG. 3C).

Given that the migration of Tr1 cells was not dependent on the presence of their specific antigen, the inventors were able to compare their migration to purified cells ex vivo. First, to make sure that the greater migration of Tr1 cells compared with Th1 cells toward the inflamed colon was not due to a relatively poor migration of the population of Th1 cells differentiated in vitro, the inventors compared the migration of the Tr1 cells with the total cell infiltration (80%; polynuclear neutrophils) or purified $CD4^+$ T cells, isolated from the inflamed colon of scid mice reconstituted with $CD4^+$ $CD45RB^{hi}$ T cells (FIG. 4A). The different cell populations were marked with different fluorescent probes and co-injected intravenously into scid mice reconstituted with $CD4^+$ $CD45RB^{hi}$ T cells four weeks earlier. Twenty-four hours after the injection, the migration of fluorescent cells toward the inflamed colon was analyzed by flow cytometry. The greater migration of Tr1 cells toward the inflamed tissue was confirmed because their migration toward the inflamed colon was three times greater than the migration of the total leukocyte population and more than 30 times greater than the migration of purified $CD4^+$ T cells isolated from the inflamed colon (FIG. 4A).

The Tr1 Cell-Specific Migration is not Limited to the Inflamed Bowel.

The injection of Tr1, Th1 and Th2 cells into untreated scid mice or normal BALB/c mice showed no specific tropism of the Tr1 cells toward normal intestinal tissue (data not shown).

For this reason, to analyze whether the Tr1 cell-specific migration in the absence of an antigen was limited to the inflamed intestinal tissue or if it was specific to the inflammatory signals present in any given tissue, the inventors constructed a skin inflammation model by applying hapten oxazolone to the skin of the ear (FIG. 5A). The inflammation was characterized by an infiltration of leukocytes (FIG. 5B) with both CD4$^+$ and CD8$^+$ T cells (not shown).

To analyze the migration of T cells in the inflamed skin, Th1, Th2 and Tr1 cells were marked with fluorescent calcein and injected 5 days after the oxazolone treatment. Similarly to the IBD model, the Tr1 cells showed a greater migration to the inflamed ear (FIGS. 5C and D) by comparison with the Th1 and Th2 cells which preferably migrated toward the draining lymph nodes and the spleen (FIGS. 5C and D). For each population, the rate of cells in a given tissue with respect to the total number of cells collected can be taken as a measurement of the relative capacity of these cells to move toward these organs. These rates differ significantly between the four populations analyzed: 90% for Tr1 cells, 60% for Th1 cells and 30% for Th2 cells in the inflamed ear, and 10% for Tr1 cells, 40% for Th1 cells and 70% for Th2 cells in the lymphoid organs (FIG. 5E). In all, the data shows that Tr1 cells migrate toward the inflamed tissue and suggests that the specialized migration of Tr1 cells is dependent on the inflammatory signals and is neither antigen-dependent nor tissue-specific.

Firm Adhesion of Tr1 Cells to Vascular Endothelial Cells Activated Under Flow Conditions Adhesion to inflamed venules is an early and essential event in the recruitment of leukocytes circulating in the direction of the inflammation site. To further examine the analysis of the mechanisms that lead to greater migration of Tr1 cells to inflamed tissue, the interaction between Tr1 and Th1 cells and activated TNF-α endothelial cells was compared. To analyze this process, the inventors performed experiments in a flow chamber coated with an activated TNF-α vascular endothelial cell line (SVEC4-10) and the adhesion of the T cells to the fluorescent marking was analyzed by video images, as described above (Ticchioni et al, FASEB J. 2001 February; 15 (2): 341-50). As regards the in vivo experiments, fluorescent stains were used to mark the Tr1 and Th1 mouse cells. The T cells were mixed in equal number and perfused on a monolayer of SVEC4-10 at a rate of 2 dyn/cm2. The results showed that the Tr1 cells had a greater capacity to stop at the activated vascular endothelial cells by comparison with the Th1 cells (FIGS. 6A and B). In similar experiments, the Th2 cells showed minimal stopping at the activated endothelial cells (not shown).

To confirm that this firm adhesion to the activated vascular endothelial cells is a mark of Tr1 cells, the inventors performed similar flow chamber experiments on human Tr1, Th1 and Th2 cells (Table 1) (Groux et al, 1997; Lecart et al, J Invest Dermatol. 2001 August; 117 (2): 318-25). The human Th1, Th2 and Tr1 cells isolated from different donors was marked with green-fluorescent fluorescein diacetate and perfused separately on a transformed human cell line previously activated by TNF-α. FIG. 8C shows that the human Tr1 cells demonstrate higher levels of firm stopping at activated endothelial cells by comparison with Th1 and Th2 cells. This result suggests that the accumulation of Tr1 cells observed in the inflamed tissue in vivo is due in part to the greater adhesion of circulating Tr1 cells to the activated endothelium.

Tr1 Cell Adhesion Mechanism.

The early event of adhesion was first analyzed, the mobile phase. The number of mobile cells during flow chamber adhesion tests was compared between different Tr1 and Th1 cells marked with fluorescent calcein. In addition, large numbers of Tr1 lymphocytes rolled on activated endothelial cells by comparison with Th1 lymphocytes (FIG. 7A). Given that P-selectin is a large molecule that causes rolling of T lymphocytes on inflamed venules in vivo (Hirata et al, J Exp Med. 2000 Dec. 4; 192 (11): 1669-76), the number of mobile Tr1 and Th1 cells on the slides coated with P-selectin was noted. The Tr1 lymphocytes showed greater capacities for rolling on the P-selectin than the Th1 cells (FIG. 7A). The greater rolling of the Tr1 cells on the slides coated with P-selectin is correlated with the higher mRNA expression of PSGL-1 (P-selectin glycoprotein-ligand-1) both on human and mouse Tr1 cells (FIGS. 8A and B). These results suggest that the overexpression of PSGL-1 on Tr1 cells plays an important role in the superior capacity of these cells to migrate toward inflamed tissue.

LFA-1/ICAM-1 and VLA-4/VCAM are important mediators of the adhesion of T cells in the inflammatory process (Alon et al, Semin Immunol. 2002 April; 14 (2): 93-104). Consequently, the contribution of both LFA-1 and VLA-4 to the increased adhesion of Tr1 cells to the activated endothelium was determined. By using adhesion tests in a flow chamber coated with recombinant ICAM-1 as a substrate, a greater adhesion of the Tr1 cells to ICAM-1 by comparison with the Th1 cells was observed. These results correspond to those obtained with activated endothelial cells, suggesting that the LFA-1/ICAM-1 interaction plays a predominant role in the adhesion of Tr1 cells to the inflamed endothelium (FIG. 7B).

The important role of LFA-1 in the adhesion of Tr1 cells was confirmed by experiments using anti-beta-2 integrin chain blocking antibodies which inhibited the stopping of Tr1 cells at the activated endothelium in flow chamber experiments (FIG. 7C) and with in vivo experiments in which the pre-incubation of Tr1 cells with ICAM-Fc molecules inhibited their migration toward the inflamed ears (FIG. 7D). By contrast with the crucial role played by LFA-1, the VLA-4/ICAM-1 interaction did not appear to be important for the adhesion of Tr1 cells because Tr1 cells do not stop at the slides coated with VCAM-1 (FIG. 7B). In addition, anti-beta1 blocking antibodies or soluble VCAM-1 did not prevent the stopping of Tr1 cells at the activated endothelium, while they inhibited the adhesion of Th1 cells (FIG. 7C).

Expression of Adhesion Molecules on Tr1 Cells

To carry out the study on the mechanisms explaining the selective migration of Tr1 cells in vivo, a complete quantitative analysis of the best-known adhesion molecules on a plurality of human and mouse Tr1, Th1 and Th2 cells (FIGS. 8A and B) was performed. In accordance with the functional studies, an overexpression of the mRNA αL and β2 integrin chains (LFA-1) on Tr1 cells was observed by comparison with the other cell populations analyzed. This result was confirmed by flow cytometry, while the expression of both the alphaL and beta2 membrane showed increased regulation on Tr1 lymphocytes by comparison with the Th1 and Th2 cells (FIG. 8C). Higher mRNA and membrane expressions of the CD31/PECAM-1 molecule was observed on the Tr1 cells (FIGS. 8A and B) by comparison with the Th1 and Th2 cells (FIG. 8B). The CD31/PECAM-1 molecule plays a crucial role in diapedesus (Liao et al, J Exp Med. 1997 Apr. 7; 185 (7): 1349-57); a higher expression of this molecule on Tr1 cells could facilitate their passage into the subendothelial compartment. The inventors also found higher expressions of genes and membranes of the two alpha V and beta3 integrin chains (FIGS. 8A, B and C) which, once dimerized, produce a fibronectin and a vitronectin receptor and other components of the extracellular matrix (Huang et al, Oncogene. 2000 Apr. 6; 19 (15): 1915-23). A higher alpha V membrane expression was also confirmed on human Tr1 cells (FIG. 8B). The high expression of alphaV/beta3 on Tr1 cells could accelerate their progression from the subendothelial compartment in the direction of the other cell compartments deep within the inflamed organ.

Discussion

The inventors thus demonstrated that Tr1 cells show a greater and selective capacity to migrate toward inflamed tissue. This migration specific to Tr1 T cells in inflamed organs as observed in vitro in two different models is not dependent on the type of tissue, because it is observed in the same way in the inflamed colon and skin, nor on the type of inflammation, whether it is induced by Cd4$^+$ Th1 T cells in the IBD model (Powrie, Immunity. 1994 October; 1 (7): 553-62) or primarily by CD8$^+$ T cells in the skin irritant model (Kehren et al, J Exp Med. 1999 Mar. 1; 189 (5): 779-86; Bour et al, Acta Derm Venereol 1995 May; 75 (3): 218-21) and is not dependent on the presence of a specific antigen. These results suggest that the inflammatory signals, generated in most tissue and in different types of immune responses, can rapidly activate the recruitment of Tr1 cells and that, in correlation with their migratory capacities, the inhibitor effect of these cells occurs locally and selectively in peripheral inflamed tissue. It is interesting to note that recent studies have indirectly confirmed these observations by using two different transplantation models: the authors showed that regulatory T cells ware enriched in tolerated grafts by comparison with secondary lymphoid tissue (Sawitzki, Transplant Proc. 2001 May; 33 (3): 2092-3; Graca, J Exp Med. 2002 Jun. 17; 195 (12): 1641-6). This selective tropism toward the peripheral inflamed organs helps to explain one of the paradoxes of the function of the regulatory T cell. Indeed, it is now clear that the regulatory T cells function via an antigen-induced mechanism in which the vicinity is suppressed, which means that the regulated and regulatory T cells must be very close but do not necessarily recognize the same antigen (Groux et al, 1997). In addition, several reports have suggested that natural regulatory T cells are directed against themselves or antigens commonly encountered (Cong et al, J. Immunol. 2002 Dec. 1; 169 (11): 6111-9). Consequently, it can be asked how protection mechanisms, which depend upon regulatory T cells, still allow the development of immune responses beneficial to pathogens in vivo. The poor migration of Tr1 cells, by comparison to Th1 and Th2 effector T cells, in the direction of secondary lymphoid organs, where the protection immune responses begin, can explain these observations.

The migration of leukocytes from the blood flow to the tissue is facilitated by a process consisting of several phases, which, in many instances, involves (i) the capture and rolling of leukocytes by selectins, (ii) the rapid activation of leukocyte integrins, (iii) the adhesion to endothelial ligands via the activated integrins and (iv) diapedesis (Kubes, Semin Immunol. 2002 April; 14 (2): 65-72. Review; Springer, Cell. 1994 Jan. 28; 76 (2): 301-14. Review; Butcher et al, Science. 1996 Apr. 5; 272 (5258): 60-6. Review). It has been shown that chemokins and chemokin receptors provide an important contribution to the chemoattraction of selective subsets of leukocytes in various tissues, but also for the activation of integrins on leukocytes in order to induce a firm stop at the activated endothelial cells (Constantin et al, Immunity. 2000 December; 13 (6): 759-69; Campbell, Science. 1988 Jan. 16; 279 (5349): 381-4). However, the analysis of the expression of chemokin receptors on Tr1, Th1 and Th2 cells shows a surprising decreased regulation in the expression of all of the chemokin receptors known on Tr1 cells, by comparison with Th1 and Th2 cells. This decreased regulation was confirmed by a reduced migration in response to the chemokins involved in inflammation (MIG) or in the migration toward the lymphoid organs (SLC and SDF-1) (Baggiolini, 1998). These results suggest that no overexpression of a particular chemokin receptor can explain the Tr1 cell-specific migration in the direction of inflammatory sites. In spite of this lack of overexpression of chemokin receptors, both human and mouse Tr1 cells show greater adhesion to activated vascular endothelial cells than Th1 and Th2 cells.

The inventors first observed that the Tr1 cells showed capacities for rolling on activated vascular endothelial cells and P-selectin under flow. A better firm stopping of Tr1 cells on activated vascular endothelial cells by comparison with Th1 lymphocytes was also observed. In the examination of these enhanced mechanisms of adhesion of Tr1 cells to activated vascular endothelial cells, it was observed that the expression of the membrane and the function of LFA-1 showed an increased regulation on Tr1 cells by comparison with other T cell subsets. The importance of the role of LFA-1 for the migration specific to Tr1 cells was confirmed in an in vivo environment where blocking LFA-1 by ICAM-Fc molecules inhibited the migration of Tr1 cells in the direction of the inflamed tissue.

In fact, a complete analysis of the expression of adhesion molecules on subsets of CD4$^+$ T cells showed that Tr1 cells overexpress a specific set of adhesion molecules which cooperate to induce their migration toward damaged tissue, PSGL-1, LFA-1, alphaV/beta3 and PECAM-1. Indeed, the overexpression of PSGL-1 increases the rolling capacity of Tr1 cells. It has been shown that LFA-1 is involved in the stopping and extravasation steps. PECAM-1 is also a molecule that plays an important role in the extravasation step, and, finally alphaV/beta3 induces the migration of cells within tissues through the extracellular matrix (Liao et al, 1997; Huang et al, 2000). It is interesting to note that, in a disputed manner with regard to the overexpression of a plurality of adhesion molecules, Tr1 cells have a reduced capacity to adhere to VCAM-1 by comparison with Th1 cells. Although the expression of VCAM-1 is induced in inflammatory sites, it has also been reported that VCAM-1 is a central molecule in the generation of humoral responses through the T-B cell interactions. The inventors thus hypothesized that the lack of VLA-4 function on the Tr1 lymphocytes can ensure that the regulatory T cells are excluded from the B cell compartment in the initiation of immune responses mediated by B cells (Leuker et al, J Exp Med. 2001 Mar. 19; 193 (6):755-68).

TABLE 1 cytokine profile of clones and populations of various T cells used

| Species | Name | Type | IL-2 (pg/ml) | IL-4 (pg/ml) | IL-10 (pg/ml) | IFN-γ (ng/ml) |
|---|---|---|---|---|---|---|
| mouse | A-10-9 | Tr1 | <40 | <50 | 1874 ± 217 | 65 ± 9 |
| mouse | A-10-11 | Tr1 | <40 | <50 | 1595 ± 184 | 42 ± 4 |
| mouse | Nice-1 | Tr1 | <40 | <50 | 1936 ± 502 | 38 ± 12 |
| mouse | Nice-2 | Tr1 | <40 | <50 | 1273 ± 298 | 51 ± 9 |
| mouse | N10-7 | Tr1 | <40 | <50 | 1659 ± 432 | 37 ± 7 |
| mouse | N10-11 | Tr1 | <40 | <50 | 1804 ± 394 | 41 ± 5 |
| mouse | N10-23 | Tr1 | <40 | <50 | 1493 ± 276 | 13 ± 3 |
| mouse | N12-4 | Th1 | 219 ± 42 | <50 | <75 | 73 ± 13 |
| mouse | N12-8 | Th1 | 275 ± 31 | <50 | <75 | 97 ± 10 |
| mouse | N12-13 | Th1 | 196 ± 54 | <50 | <75 | 84 ± 17 |
| mouse | N4-2 | Th2 | <40 | 912 ± 81 | 305 ± 49 | <1 |
| mouse | N4-9 | Th2 | <40 | 1065 ± 103 | 287 ± 36 | <1 |
| mouse | N4-12 | Th2 | <40 | 715 ± 59 | 412 ± 67 | <1 |
|  | Pop.Tr1 |  |  | <20 | 112 ± 19 | 12865 ± 1457 | 5 ± 0.1 |
|  | Pop.Tr1 |  |  | <20 | 86 ± 21 | 14945 ± 1065 | 2.8 ± 0.2 |
|  | Pop.Th1 |  |  | 513 ± 106 | <40 | 11045 ± 984 | 156 ± 4 |
|  | Pop.Th1 |  |  | 312 ± 95 | <40 | 16321 ± 1203 | 124 ± 15 |
|  | Pop.Th2 |  |  | <20 | 2321 ± 769 | 12378 ± 834 | <0.2 |
|  | Pop.Th2 |  |  | <20 | 998 ± 143 | 13241 ± 984 | <0.2 |
| human | JDV15 | Tr1 | <20 | <40 | 12865 ± 1457 | 4 ± 0.2 |
| human | JDV308 | Tr1 | <20 | <40 | 14945 ± 1065 | 3.1 ± 0.3 |
| human | BJF161 | Tr1 | <20 | <40 | 11045 ± 984 | 2.6 ± 0.2 |
| human | HA-IAJ2 | Tr1 | <20 | <40 | 16321 ± 1203 | 2.1 ± 0.1 |
| human | HA-IE7 | Tr1 | <20 | <40 | 12378 ± 834 | 1.5 ± 0.2 |
| human | HA-2D5 | Tr1 | <20 | <40 | 13241 ± 984 | 0.8 ± 0.1 |
| human | JDV305 | Th1 | 523 ± 41 | <40 | 239 ± 98 | 8.3 ± 0.6 |
| human | BJF180 | Th1 | 613 ± 74 | <40 | 329 ± 274 | 9.2 ± 0.7 |
| human | HAT203 | Th1 | 712 ± 65 | <40 | 121 ± 32 | 7.9 ± 0.8 |
| human | BJF116 | Th2 | <20 | 1234 ± 96 | 2345 ± 175 | <0.5 |
| human | PUEF39 | Th2 | <20 | 863 ± 71 | 3059 ± 234 | <0.5 |
| human | BJF157 | Th2 | <20 | 1457 ± 102 | 2019 ± 124 | <0.5 |

The T cell clones and the human and mouse T cell populations are generated as described above. The murine T cells were stimulated with the OVA peptide (0.6 μM) and total irradiated splenocytes ($2 \times 10^6$ cells/ml). The cytokines were analyzed by ELISA in culture supernatants collected after 24 h for IL-2 and IL-4 and after 48 h for IL-10 and IFN-γ. The human T cell clones were activated with cross-linked monoclonal antibodies anti-CD3 (10 μg/ml) and anti-CD28 (1 μg/ml), the supernatants were collected after 24 h for IL-2 and IL-4 and after 48 h for IL-10 and IFN-γ. The results show combined data from 3 representative experiments.

Example 5

Method for Preparation of T Cells and Dendritic Cells for the Characterization of CD4$^+$ CD18b$^{bright}$CD49b$^+$ Tr1 Cells Experimental Procedures Mice The BALB/cAnN mice were obtained from CERJ (Le Genest Saint Isle, France), the DO11-10 homozygous mice were generously donated by Dr. S. D. Hurst (DNAX Research Institute, Palo Alto, Calif.). The BALB/c IL-10 transgenic mice were obtained using cDNA hIL-10 under the control of the MHC class II Ea promoter 10. All of the animals were raised under standard aseptic conditions in our animal facility. All of the mice were female, 4 to 8 weeks old, at the beginning of each experiment.

Medium, Antibody and Reagents

The medium used for the T cell cultures was the Yssel medium (Yssel et al, 1984). The dendritic cells were cultivated in RPMI 1640 supplemented with 10% SVF (Roche, Meylan, France), 2 mM of L-glutamine, 1% sodium pyruvate, $2 \times 10^{-5}$ M β2-mercaptoethanol (all of Invitrogen). For the purification of the dendritic cells, the inventors used the HESS medium without Ca$^{++}$ and Mg$^{++}$ containing 2 mM of EDTA (all of Invitrogen) and collagenase D (Roche, Meylan, France).

The recombinant mouse GM-CSF, TNF-α, and IFN-γ came from R&D Systems, Abington, UK. The recombinant mouse IL-10 and IL-4 were generously provided by Dr. R. L. Coffman, DNAX Research Institute, Palo Alto, Calif.

The purification and characterization of the DC were performed by means of antibodies anti-CD3 (17A2), anti-CD4 (GK1.5), anti-CD8 (53-6.7), anti-CD11b (M1/70), anti-CD11c (HL3), CD28 (37.51) anti-I-Ad (AMS-32.1), anti-CD62L (Mel-14), anti-CD80 (16-10A1), anti-CD86 (GL1), anti-B220 (RA3-6B2), CD45RB (16A), anti-Gr1 (RB6-8C5) (all of Pharmingen Becton Dickinson) and DEC-205 (NLDC-145) (Serotec, UK).

The cytokine assays were performed by means of purified antibodies anti-IL-4-PE or -FITC (11B11), anti-IFN-γ-PE (XGM1.2), anti-IL-10-FITC (JES-16E3), anti-IL-4 (11B11) and anti-IL-10 (2A5), anti-IFN-γ (XGM1.2) and biotinylated antibodies anti-IL-4 (24G2), anti-IL-10 (SXC1), anti-IFN-γ (R4-6A2) (all of Pharmingen Becton Dickinson).

The antibodies anti-IgE (R35-72) and anti-IgG1 (A85-1) used for the analysis of OVA-specific serum IgG were of Pharmingen Becton Dickinson.

The lysis buffer, metrizamide, LPS, the OVA$_{323-339}$ peptide, ovalbumin and alun were of Sigma, Saint Quentin Fallavier, France.

Flow Cytometry

The phenotype analysis of the DC subsets was performed by double or triple staining with biotinylated antibodies anti-CD11c, followed by streptavidin-Cy-Chrome, anti-CD45RB coupled to PE and a third antibody coupled to FITC. All of the staining steps were conducted at 4° C. in the PBS buffer with 0.1% SAB and 0.02 mM of NaN3. After three washings, the marked cells were analyzed on a FACScan (Becton Dickinson).

Staining of Intracellular Cytokines

The analysis of intracellular cytokines by flow cytometry was performed as described (Groux et al., 1997). The cells ($10^6$/ml) were activated for 6 h with immobilized anti-CD3 and anti-CD28 ACm. The monensin was added at 10 µg/ml and 4 h later, the cells were harvested, washed and fixed in formaldehyde at 2%. For the intracellular staining, the cells were incubated with the following ACms: anti-IL4-FITC or -PE, anti-IFN-γ-PE and anti-IL-10-FITC, or controls of a corresponding isotype, all at 5 µg/ml. The samples were analyzed on a FACScan (Becton Dickinson).

Dendritic Cells Derived from Bone Marrow (DC-MO)

The DC-MO were generated from medullary progenitors, as described above, with several modifications (Inaba et al., 1992). In short, the bone marrow was extracted by rinsing tibias and femurs before removing the red blood cells with 0.83% ammonium chloride. The cells were cultivated at 37° C., on 24-well plates (Becton Dickinson) ($10^6$ cells/ml/well), in the complete RPMI medium supplemented with 10 ng/ml of recombinant murine GM-CSF and 2.5 ng/ml of recombinant murine TNF-α, with or without recombinant murine IL-10 (500 ng/ml). The DC-MO were harvested on D6.

Purification of Splenic Dendritic Cells

Spleens were cut into small fragments which were digested by collagenase D (1 mg/ml) in HESS for 20 nm at 37° C., under constant agitation. The digested fragments were filtered on a screen of 0.7 µm (Becton-Dickinson) and the cell suspension was washed twice in the purification medium. The cells were then deposited in a layer on a metrizamide gradient and centrifuged at 600 g for 10 min. The cells concentrated at the interface were collected, washed once and returned to the suspension in the purification medium, in order to separate the DC from the lymphocytes. The different T cell lines, the B cells and the granulocytes were depleted by treating the collected low-density cells, for 30 min at 4° C., with a mixture of monoclonal antibodies composed of anti-CD3, anti-B220 and anti-GR-1. The positive cells were collected magnetically, after incubation for 1 h at 4° C. with magnetic beads coated with anti-rat Ig, in a ratio of 10 beads to 1 cell.

Preparation of "Virgin" Transgenic TCR T Cells

Splenic T cells of DO11.10 OVA TCR transgenic mice were prepared as previously described (Groux et al., 1997). In short, CD4+ T cells were enriched by negative selection using magnetic beads with a mixture of ACm anti-CD8, anti-B220 and anti-CD11b. The CD4$^+$/Mel14$^{bright}$ T cells were then sorted by flow cytometry using antibodies anti-CD4-PE and anti-CD62L-FITC (Mel14). The T cell populations sorted were typically positive at 99% for the two markers.

Differentiation of TCR Transgenic T Cells by Dendritic Cells

The in vitro T cell differentiation tests were performed in the Yssel medium. The primary stimulation cultures were established by activating purified "virgin" CD4+ T cells (2.5× $10^5$) by dendritic cell populations which were sorted, pulsed with the OVA$_{323-339}$ peptide (0.6 µM) in a total volume of 1 ml, on 24-well plates (Becton Dickinson). The cells were then multiplied, harvested at D7, washed three times, counted and restimulated by freshly sorted dendritic cell populations+ 0.3 µM of OVA$_{323-339}$ peptide for the second differentiation. The same procedure was applied for the third differentiation cycle. After the differentiation, the T cells were harvested, washed and restimulated with 0.3 µM of OVA$_{323-339}$ and splenic CPA were irradiated. The proliferation of T cells was measured by incorporating $^3$H-thymidine for the final 12 hours of the 72-hour incubation. The production of IL-4, IL-10 and IFN-γ was measured by ELISA in the supernatants collected 48 h after the restimulation of T cells.

Transwell Experiments

In the lower compartment of a transwell system (0.4 µM Costar-Dutscher, Brumath, France), $10^6$ purified CD4+ T cells isolated from normal BALB/c mice were stimulated with $10^6$ irradiated splenocytes of BALB/c mice and ACm anti-CD3 (10 µg/ml). In the upper compartment, CD4+ T cells differentiated by a single stimulation with dendritic cells were stimulated with 0.3 µM of OVAp and $10^6$ irradiated splenocytes. Three days later, the slide tray was removed and the T cells of the lower wells were transferred (in triple) to 96-well plates. The proliferative response was analyzed by the incorporation of $^3$H-thymidine in the final 12 hours of the culture.

Cytology

The sorted CD11c$^{low}$CD45RB$^+$ and CD11c$^{high}$CD45RB$^-$ generated in vitro or isolated from BALB/c mouse spleens, were incubated for 24 h with LPS (1 µg/ml) in the presence of GM-CSF (10 ng/ml). The freshly sorted or stimulated DC were centrifuged (Cytospin2, Shandon) and stained with May-Grünwald-Giemsa.

Real-Time Quantitative RT-PCR Assay

The total RNA of the subsets of sorted DC (1×$10^6$; purity >99%) was prepared with TRIZOL (Life Technologies), as previously described (Cottrez et al., 1994), and any possible trace of contaminating chromosomal DNA was digested by DNase I, according to the manufacturer's instructions (Gene Hunter, Nashville, Tex.). Then, the RNA was subjected to reverse transcription with an oligo(dT)12-18 and Superscript II reverse transcriptase (Life Technologies), as previously described (Cottrez et al., 1994). The real-time quantitative PCR was performed with the SYBR Green PCR Core Reagents Kit, on special microtitration plates, with 96 wells (Applied Biosystems, Courtaboeuf, France) in an ABI PRISM 5700 Sequence Detection System apparatus (Applied Biosystems), according to the manufacturer's instructions. The fluorescence signals were generated in each PCR cycle by direct incorporation of SYBR Green in the double-strand DNA chain, to give quantitative information in real time. Primers (MWG Biotech, Ebersberg, Germany) encompassing the exon-intron junctions were designed to prevent the amplification of genomic DNA and to give amplicons of 100 to 150 pb, so as to enhance the efficiency of the amplification by PCR. All of the primers were used under conditions that prevented the formation of dimers, and the reliability of the amplification products was verified by electrophoresis and enzymatic restriction maps. All of the cDNA were assayed on the value of the average expression of 4 different housekeeping genes. The experimental conditions of the PCR were as follows: 10 nm at 94° C., and 40 cycles of 30 s at 94° C., 30 s at 60° C. and 30 s at 72° C. for each amplification, in a final volume of 20 µl. The target gene expression was measured, after normalization of RNA concentrations, with the 4 housekeeping genes and the values are expressed in terms of factors increasing the expression with respect to a negative control Cytokine Assay IL-4, IL-10 and IFN-γ were assayed using an ELISA sandwich method as previously described (Cottrez et al., 2000). In short, ELISA plates (Polylabo, France) were coated with suitable anti-cytokine ACm in a carbonate buffer and incubated at 4° C. for one night. The reactions were blocked for 30 min at room temperature with 150 µl of PBS/SVF at 20 in each well; 50 µl of diluted supernatants of CD4+ T cells stimulated in vitro were then added to the wells, before incubating the plates at 4° C. for one night. After a washing step, 50 µl of biotinylated antibody of the second step were added to each well. The plates were incubated for 1 h at room temperature and washed. The enzymatic conjugate (streptavidin-peroxidase) was then added to each well. The plates were then incubated at room temperature for 1 h, washed, and 100 µl of substrate (ABTS, 1 mg/ml) were added to each well. The plates were read on an ELISA reader at 405 nm, after formation of the color (Labsystems iEMS reader, Helsinki, Finland).

IL-10 Induces the Differentiation of a Distinct DC Subset.

It is known that IL-10 induces the differentiation of Tr1 cells by an indirect effect (Wakkach et al., 2001). Given that DCs play an essential role in the differentiation of T cells, the inventors analyzed the effect of IL-10 on the differentiation of DCs from bone marrow progenitor cells cultivated in the presence of GM-CSF and TNF-α (the preliminary experiments showed that the presence of TNF-α does not influence the phenotype and the function of DC, but nevertheless helps to increase the yield and viability of dendritic cell populations [data not shown]). The addition of IL-10 on day 0 of the culture induced the differentiation of a DC population with a low expression of CD11c and a high expression of CD45RB (FIG. 9A). However, in the absence of IL-10, the addition of GM-CSF and TNF-α induced the differentiation of DC expressing high concentrations of CD11c (FIG. 9A) (Inaba et al., 1992). After sorting cells by FACS according to the specific expression of CD11c and CD45RB, the CD11c$^{low}$CD45RB$^+$ DC differentiated in vitro had a plasmacytoid morphology, with a smooth plasmic membrane and an excentric nucleus (FIGS. 9B-1). However, the CD11c$^{high}$ DC had a different morphology, with the presence of small dendrites (FIGS. 9B-3). After a new maturation with LPS, the two populations acquired a morphology of fully mature DCs, with long dendrites (FIGS. 9B-2 and 4). The analysis of the expression of MHC II molecules and co-stimulators showed low levels of expression of CD80, CD86 and I-A on CD11c$^{low}$CD45RB$^+$ DC (FIG. 9C) with respect to CD11c$^{high}$ DC. The maturation of dendritic cells with LPS did not modify the phenotype of CD11c$^{low}$CD45RB$^+$ DC (FIG. 9C), while it reinforced the expression of molecules CD80, CD86 and I-A on CD11c$^{high}$ DC. These results show that IL-10 induces the differentiation of a distinct subset of DC characterized by the specific expression of CD45RB, which have a pseudo-immature phenotype that cannot be modified by stimulation with LPS.

Isolation of the Natural Equivalent of DCs Derived from IL-10

The inventors therefore addressed the question of the influence of IL-10 in vivo on the differentiation of dendritic cells. Enriched splenic DCs isolated from Tg IL-10 non-transgenic mice or BALB/c mice were analyzed for the expression of a marker specific to CD11c murine DCs (FIG. 10A). In Tg IL-10 mice, a large number of DCs weakly expressing CD11c was observed with respect to normal BALB/c mice (FIG. 10A) or the non-transgenic controls (data not shown). As for the CD11c$^{low}$ DCs differentiated in vitro in the presence of IL-10, the splenic CD11c$^{low}$ DCs strongly expressed the CD45RB marker (FIG. 10B). In addition, the DCs derived in vitro and the splenic CD11c$^{low}$CD45RB$^+$ DCs both had a plasmacytoid morphology (FIG. 10C-1), unlike the CD11c$^{high}$ DCs which had small dendrites (FIGS. 10C-3). After complete maturation with LPS, the two splenic DC populations differentiated into fully mature DCs with long dendrites (FIGS. 10C-2 and 4).

The inventors then studied the expression of I-A$^d$ molecules of the MHC and co-stimulators CD80 and CD86 on splenic CD11c$^{low}$CD45RB$^+$ and CD11c$^{high}$CD45RB$^-$ DCs sorted on FACS, from Tg IL-10 mice and BALB/c control mice. As shown in FIG. 10D, it has been noted that purified CD11c$^{low}$CD45RB$^+$ DCs ex vivo weakly expressed the molecules of class II MHC, CD80 and CD86, with respect to CD11c$^{high}$CD45RB$^-$ DCs. To determine whether the CD11c$^{low}$CD45RB$^+$ DCs represent a distinct DC subset and the product of a separate developmental line, or whether they represent a more conventional immature DC stage, the in vitro maturation of isolated DCs was induced by short-term cultures in the presence of GM-CSF (in order to increase the lifetime and recovery rate) and LPS. Under these conditions, after in vitro maturation with LPS, the CD11c$^{low}$CD45RB$^+$ DCs still retained a low expression of molecules of class II MHC and CD86, which suggests that their pseudo-immature phenotype is stable, with the exception of the overexpression of CD80. However, after in vitro incubation with LPS, the CD11c$^{high}$CD45RB$^-$ DCs show an increased maturation, with an increase in the expression of class II MHC molecules and two co-stimulators (CD80 and CD86) (FIG. 10D). Overall, these results show that the CD11c$^{low}$CD45RB$^+$ DCs isolated from the spleen represent equivalents in vivo of DCs derived from IL-10.

Phenotypic Characterization and Secretion of Cytokines of the CD11c$^{high}$CD45RB$^+$ Dendritic Cell Subset.

To better characterize the CD11c$^{low}$ CD45RB$^+$ DC subset, the inventors analyzed the expression of different dendritic cell markers on the sorted CD11c$^{low}$CD45RB$^+$ and CD11c$^{high}$CD45RB$^-$ cell populations from BALB/c mice (FIG. 11A). The CD11c$^{low}$CD45RB$^+$ and CD11c$^{high}$CD45RB$^-$ DCs weakly express CD11b and DEC 205 and do not express CD8α at all, which suggests that they do not belong to the "standard" line of myeloid (CD11c$^{high}$) or lymphoid (CD8α$^+$) DCs (Shortman and Liu, 2002). Moreover, unlike a population of recently described DC differentiated from a B cell precursor, the CD11c$^{low}$CD45RB$^+$ DCs are negative in B220 (Lu et al., 2001; Martin et al., 2002). Finally, these cells do not express the markers specific to T cells (CD4 and CD2) (data not shown).

An important part of the specific function of DCs is dictated by the secretion of distinct sets of cytokines. The inventors therefore analyzed, by quantitative RT-PCR, the relative expression of several important cytokines on CD11c$^{low}$CD45RB$^+$ and CD11c$^{high}$CD45RB$^-$ dendritic cells freshly sorted or activated by LPS. After activation by LPS, the CD11c$^{low}$CD45RB$^+$ DCs secreted IL-10 while the CD11c$^{high}$CD45RB$^-$ DCs secreted IL-12. Both populations showed a secretion of IL-1β, further increased by the activation by LPS, but did not secrete IFN-α, even after 24 h of activation by LPS (FIG. 11B). These results show that the CD11c$^{low}$CD45RB$^+$ DCs represent a distinct subset of dendritic cells that secrete primarily IL-10 after activation.

CD11c$^{low}$CD45RB$^+$ DCs Differentiate Tr1 Cells In Vitro

To analyze the influence of the various DC subsets on the priming and the differentiation of specific T cells never exposed to OVA ("virgin") isolated from DO11-10 mice, several T-cell stimulation cycles were established with sorted CD11c$^{low}$CD45RB$^+$ or CD11c$^{high}$CD45RB$^-$ DCs isolated from the spleen of BALB/c mice (FIG. 12A) or differentiated in vitro (FIG. 12B). The purified "virgin" CD4+ T cells were stimulated by OVA (0.6 µM), at different DC/T ratios, for one week. Then the T cells were harvested, washed and stimulated again, under the same conditions, with 0.3 µM of OVA. After a third stimulation under the same conditions, the polarized T cell populations were collected, washed and restimulated with irradiated splenocytes of BALB/c mice and 0.3 µM of OVA in order to analyze their cytokine profile (FIG. 12A). Our results show that the CD11c$^{low}$CD45RB$^+$ DCs purified ex vivo or differentiated in vitro, regardless of the DC/T ratio used, induced the differentiation of Tr1 cells secreting IL-10 strongly, IFN-γ weakly and no IL-4 (or in negligible amounts) (Groux et al., 1997) (FIGS. 12 A and B). Unlike the CD11c$^{low}$CD45RB$^+$ dendritic cells, those of the CD11c$^{high}$CD45RB$^-$ subset primed the Th1 cells that strongly secreted IFN-γ (FIGS. 12A and B). These results correspond to the cytokine profile of the dendritic cell subpopulation, i.e. CD11c$^{low}$CD45RB$^+$, which differentiate Tr1 cells, secrete IL-10, while the IL-12 secreted by CD11c$^{high}$CD45RB$^-$ DCs induces the differentiation of Th1 cells.

In addition, the specific differentiation of Tr1 cells with CD11c$^{low}$CD45RB$^+$ DCs was observed after a single stimulation, as shown by the intracytoplasmic analysis of cytokine secretion in the different T cell sub-populations (FIG. 12C). To analyze the functional properties of T cells obtained after a single stimulation by CD11c$^{low}$CD45RB$^+$ DCs, transwell experiments were conducted. The T cells obtained after stimulation by CD11c$^{low}$CD45RB$^+$ DCs of BALB/c mice inhibited the proliferation of bystander CD4+ T cells stimulated by irradiated splenocytes and a monoclonal anti-CD3 antibody (FIG. 12D). However, the addition of ACm inhibitors of mouse anti-IL-10 and anti-TGFβ removed the suppressor effect of these T cells, confirming the phenotypic and functional differentiation of Tr1 cells (FIG. 12D). As a control, Th1 cell populations (induced by CD11c$^{high}$CD45RB$^-$ DCs) had no inhibiting effect on the proliferation of bystander CD4+ T cells (FIG. 12D). Overall, these results show that CD11c$^{low}$CD45RB$^+$ DCs induce the differentiation of Tr1 cells in vitro.

Human Cells

Dendritic cells were differentiated from progenitor cells CD34+ with GM-CSF and IL-4 in the presence or in the absence of IL-10, as shown.

After 6 days, the dendritic cells were sorted according to the expression of CD11c and marked with the antibodies indicated.

The purified cells were also stimulated with LPS for 24 hours, then analyzed by cytofluorometry.

The tolerogenic dendritic cells differentiated in the presence of IL-10 expressed low levels of CD11c, and low levels of HLA-DR, CD80 and CD86 molecules.

The activation with LPS did not increase the expression of HLA-DR and CD86 for this population, unlike the effect of LPS on the other DC populations tested.

TABLE effect of the activation of LPS on the populations of sorted dendritic cells differentiated in the presence or absence of IL-10.

| | Stimulation | | | | | | | |
|---|---|---|---|---|---|---|---|---|
| | — | — | LPS | LPS | — | — | LPS | LPS |
| | Differentiation | | | | | | | |
| | — | — | — | — | IL-10 | IL-10 | IL-10 | IL-10 |
| | CD11c low | CD11c hi | CD11c low | CD11c hi | CD11c low | CD11c hi | CD11c low | CD11c hi |
| Percentage of positive cells | | | | | | | | |
| CD14 | 12 ± 3 | 14 ± 4 | 12 ± 4 | 13 ± 3 | 15 ± 3 | 9 ± 2 | 13 ± 3 | 13 ± 3 |
| CD4 | 4 ± 2 | 3 ± 1 | 3 ± 2 | 2 ± 1 | 4 ± 1 | 5 ± 3 | 5 ± 2 | 3 ± 2 |
| CD11b | 13 ± 1 | 24 ± 8 | 23 ± 6 | 21 ± 8 | 19 ± 6 | 21 ± 4 | 18 ± 5 | 15 ± 6 |
| HLA-DR | 75 ± 12 | 80 ± 9 | 91 ± 15 | 89 ± 12 | 50 ± 8 | 85 ± 12 | 52 ± 6 | 92 ± 12 |
| CD80 | 24 ± 5 | 28 ± 6 | 80 ± 13 | 73 ± 12 | 14 ± 2 | 26 ± 11 | 45 ± 12 | 84 ± 7 |
| CD86 | 53 ± 6 | 54 ± 5 | 84 ± 15 | 79 ± 123 | 26 ± 4 | 54 ± 9 | 28 ± 6 | 73 ± 11 |
| CD40 | 81 ± 9 | 94 ± 2 | 98 ± 12 | 96 ± 11 | 74 ± 8 | 81 ± 15 | 82 ± 13 | 95 ± 11 |
| Average fluorescence intensity | | | | | | | | |
| CD14 | 250 ± 130 | 320 ± 110 | 210 ± 150 | 350 ± 80 | 210 ± 180 | 350 ± 87 | 250 ± 130 | 390 ± 102 |
| CD4 | 80 ± 63 | 86 ± 38 | 91 ± 58 | 86 ± 27 | 70 ± 53 | 83 ± 48 | 91 ± 54 | 75 ± 52 |
| CD11b | 370 ± 356 | 350 ± 256 | 367 ± 298 | 357 ± 241 | 324 ± 293 | 360 ± 255 | 357 ± 297 | 354 ± 291 |
| HLA-DR | 470 ± 570 | 590 ± 350 | 890 ± 480 | 981 ± 210 | 310 ± 150 | 520 ± 350 | 350 ± 218 | 846 ± 520 |
| CD80 | 134 ± 102 | 290 ± 130 | 357 ± 150 | 481 ± 213 | 102 ± 80 | 198 ± 97 | 283 ± 110 | 435 ± 115 |
| CD86 | 400 ± 270 | 595 ± 600 | 813 ± 370 | 789 ± 483 | 254 ± 130 | 587 ± 480 | 312 ± 178 | 834 ± 420 |
| CD40 | 320 ± 230 | 580 ± 256 | 680 ± 269 | 710 ± 297 | 367 ± 260 | 539 ± 230 | 340 ± 264 | 730 ± 260 |

The invention claimed is:

1. A method for identifying Tr1-regulatory lymphocytes present in a biological sample comprising lymphocytes, the method comprising:

a) determining a simultaneous presence of expression products of genes encoding the CD4 molecule and all of the molecules of group A by said lymphocytes, wherein said group A is selected from the group consisting of A) CD18 and CD11a, and CD49b molecules, B) CD18 and CD49b molecules and C) CD11a and CD49b; and b) identifying, as the Tr1-regulatory lymphocytes, the lymphocytes that simultaneously express the genes.

2. The method according to claim 1, wherein:

said determining comprises comparing an expression of at least one gene selected from the genes encoding the molecules of the group B consisting of CD11a, CD18, PSGL-1, PECAM-1 and alphaV/beta3, by said lymphocytes to an expression of at least one gene selected from the genes encoding the molecules of the group B consisting of CD11a, CD18, PSGL-1, PECAM-1 and alphaV/beta3, by Th1 lymphocytes or Th2 lymphocytes; and said identifying comprises identifying, as Tr1-regulatory lymphocytes, of the lymphocytes that overexpress said at least one gene.

3. The method according to claim 2, wherein said comparing comprises comparing the expression of at least two of said genes encoding the molecules of the group B and wherein said identifying comprises identifying as Tr1-regulatory lymphocytes, the lymphocytes that overexpress said two genes.

4. The method according to claim 3, wherein said comparing comprises comparing the expression of all of the genes encoding the molecules of the group B and wherein said identifying comprises identifying, as Tr1-regulatory lymphocytes, the lymphocytes that overexpress said all of the genes.

5. The method according to claim 1, wherein said determining, additionally and simultaneously, the presence of the expression product by said lymphocytes of the gene encoding the CD3 molecule and in that step (b) consists of identifying, as Tr1-regulatory lymphocytes, the lymphocytes that also simultaneously express the gene encoding the CD3 molecule.

6. The method according to claim 1, wherein said determining is performed at the surface of said lymphocytes.

7. The method according to claim 6, wherein said determining is performed using antibodies specific to said molecules.

8. The method according to claim 7, wherein each of said antibodies is marked with a marker.

9. The method according to claim 8, wherein said marker is different for each of said antibodies, and said marker is selected from the group consisting of a fluorescent marker, an enzyme marker, a chemiluminescent marker, a bioluminescent marker and a radioactive marker.

10. The method according to claim 8, wherein said markers are fluorescent markers selected from the group consisting of fluorescein isothiocyanate (FITC), or allophycocyanin (APC), phycoerythrin-cyanin 5 (PC5), phycoerythrin (PE), green fluorescent fluorescein diacetate, calcein AM and red fluorescent tetramethyl rhodamine.

11. The method according to claim 6, wherein said determining is implemented by flow cytometry.

12. The method according to claim 11, wherein said determining, for the CD18 molecule, comprises determining the presence of a CD 18 bright fluorescence intensity.

13. The method according to claim 12, wherein:

said comparing is carried out by comparing an amount of mRNA expressed for said gene; and wherein said identifying comprises identifying, the lymphocytes that overexpress the mRNA of said gene.

14. The method according to claim 13, wherein the amount of mRNA is measured by quantitative RT-PCR.

15. The method according to claim 1 wherein the biological sample is from a peripheral blood sample or an inflammatory organ in a subject.

16. The method according to claim 15, wherein the subject is affected or not affected by an autoimmune or inflammatory disease.

17. The method according to claim 16, wherein said subject has Crohn's disease or multiple sclerosis.

18. The method according to claim 1 further comprising obtaining the biological sample from in vitro preparation of Tr1-regulatory lymphocytes using a lymphocyte population of from a sample of a subject.

19. The method according to claim 18, said obtaining comprises activating CD4+ T lymphocytes of said lymphocyte population in the presence of an antigen and interleukin 10.

20. The method according to claim 18, wherein said obtaining comprises:

(i) obtaining a biological sample containing artificial antigen-presenting cells that express a molecule of the HLA class-II system and a human LFA-3 molecule and that do not express any of co-stimulation molecules B7-1, B7-2, B7-H1, CD10, CD23 or ICAM-1;

(ii) activating, in vitro, CD4+ T lymphocytes of said lymphocyte population in the presence of the selected antigen, presented by said artificial antigen-presenting cells; and (iii) collecting, from said lymphocyte population, activated CD4+ lymphocytes comprising at least 10% Tr1 lymphocytes specific to the selected antigen.

21. The method according to claim 18, wherein said obtaining comprises:

(i) obtaining, in vitro, a population of human progenitor cells capable of differentiating into dendritic cells;

(ii) placing said human progenitor cells in a culture in the presence of IL-10 so as to obtain a population of said dendritic cells; and (iii) placing said human lymphocyte population in the presence of the dendritic cells.

22. The method according to claim 1, wherein the expression products are mRNAs, and wherein said determining is performed by RT-PCR.

23. A method for quantification of Tr1-regulatory lymphocytes present in a biological sample comprising lymphocytes, comprising:

(a) determining a simultaneous presence of expression products of genes encoding the CD4 molecule and all of the molecules of group A by said lymphocytes, wherein said group A is selected from the group consisting of A) CD18 and CD11a, and CD19b molecules, B) CD18 and CD19b molecules and C) CD11a and CD19b;

(b) identifying, as the Tr1-regulatory lymphocytes, the lymphocytes that simultaneously express the genes;

(c) determining the proportion of the Tr1-regulatory lymphocytes with respect to the total amount of the lymphocytes or a particular fraction of the lymphocytes, present in said biological sample.

24. A method for in vitro prognosis or diagnosis of an autoimmune or inflammatory disease in a tested subject, using a biological sample previously taken from said tested subject, comprising:

(a) determining a simultaneous presence of expression products of genes encoding the CD4 molecule and all of the molecules of group A by lymphocytes in said biological sample, wherein said group A is selected from the group consisting of A) CD18 and CD11a, and CD19b molecules, B) CD18 and CD19b molecules and C) CD11a and CD19b;

(b) identifying, as the Tr1-regulatory lymphocytes, the lymphocytes that simultaneously express the genes;

(c) determining the proportion of the Tr1-regulatory-lymphocytes present in said biological sample with respect to the total amount of the lymphocytes or a particular fraction of the lymphocytes; and (d) comparing the proportion of said Tr1-regulatory lymphocytes with that in a biological sample taken from a subject who does not have an autoimmune or inflammatory disease.

25. The method according to claim 24, wherein said proportion is reduced in the tested subject compared to the subject who does not have an autoimmune or inflammatory disease.

26. A method for enrichment of Tr1-regulatory lymphocytes present in a biological sample comprising lymphocytes, comprising:

(a) determining a simultaneous presence of expression products of genes encoding the CD4 molecule and all of the molecules of group A by said lymphocytes, wherein said group A is selected from the group consisting of A) CD18 and CD11a, and CD19b molecules, B) CD18 and CD19b molecules and C) CD11a and CD19b;

(b) identifying, as the Tr1-regulatory lymphocytes, the lymphocytes that simultaneously express the genes;

(c) removing lymphocytes that do not simultaneously express said molecules from said sample to obtain an enrichment of Tr1-regulatory lymphocytes.

27. A method for treating an autoimmune or inflammatory disease, comprising administering to a patient in need thereof a population of Tr1 regulatory lymphocytes enriched by the method of claim 26.

28. The method of claim 27, wherein said administering is at an area of inflammation.

29. The method of claim 27, wherein the Tr1 regulatory lymphocytes are administered with an antigen capable of activating said lymphocytes in vivo.

30. The method of claim 27, wherein said Tr1 regulatory lymphocytes are lymphocytes activated in vitro or in vivo.

* * * * *